United States Patent
Bringoltz et al.

(10) Patent No.: US 10,591,406 B2
(45) Date of Patent: Mar. 17, 2020

(54) SYMMETRIC TARGET DESIGN IN SCATTEROMETRY OVERLAY METROLOGY

(71) Applicant: KLA-Tencor Corporation, Milpitas, CA (US)

(72) Inventors: Barak Bringoltz, Rishon le Tzion (IL); Daniel Kandel, Aseret (IL); Yoel Feler, Haifa (IL); Noam Sapiens, Bat Yam (IL); Paykin Irina, Haifa (IL); Alexander Svizher, Haifa (IL); Meir Aloni, Herzliya (IL); Guy Ben Dov, Haifa (IL); Hadar Shalmoni, Beit Oved (IL); Vladimir Levinski, Migdal Ha'emek (IL)

(73) Assignee: KLA-Tencor Corporation, Milpitas, CA (US)

(*) Notice: Subject to any disclaimer, the term of this patent is extended or adjusted under 35 U.S.C. 154(b) by 0 days.

(21) Appl. No.: 15/092,329

(22) Filed: Apr. 6, 2016

(65) Prior Publication Data
US 2016/0216197 A1 Jul. 28, 2016

Related U.S. Application Data

(60) Division of application No. 14/161,398, filed on Jan. 22, 2014, now Pat. No. 9,739,702, which is a
(Continued)

(51) Int. Cl.
*G01B 11/27* (2006.01)
*G01N 21/01* (2006.01)
(Continued)

(52) U.S. Cl.
CPC ........... *G01N 21/01* (2013.01); *G01B 11/272* (2013.01); *G02B 27/4255* (2013.01);
(Continued)

(58) Field of Classification Search
CPC ............ G01N 21/01; G01N 2201/068; G01N 21/9501; G01N 21/4788; G01N 21/956;
(Continued)

(56) References Cited

U.S. PATENT DOCUMENTS 5,298,939 A * 3/1994 Swanson ............. G03F 7/70275
355/30
5,333,050 A 7/1994 Nose et al.
(Continued)

FOREIGN PATENT DOCUMENTS

EP 1601931 12/2005
WO 2004076963 9/2004

*Primary Examiner* — Mohamed K Amara
(74) *Attorney, Agent, or Firm* — Suiter Swantz pc llo

(57) ABSTRACT

Metrology methods, systems and targets are provided, which implement a side by side paradigm. Adjacent cells with periodic structures are used to extract the overlay error, e.g., by introducing controllable phase shifts or image shifts which enable algorithmic computation of the overlay. The periodic structures are designed to exhibit a rotational symmetry to support the computation and reduce errors.

20 Claims, 24 Drawing Sheets

Related U.S. Application Data continuation of application No. PCT/US2013/065527, filed on Oct. 17, 2013.

(60) Provisional application No. 61/745,981, filed on Dec. 26, 2012, provisional application No. 61/715,603, filed on Oct. 18, 2012.

(51) Int. Cl.
| | |
|---|---|
| *G03F 7/20* | (2006.01) |
| *G02B 27/42* | (2006.01) |
| *G01N 21/47* | (2006.01) |
| *G01N 21/95* | (2006.01) |
| *G01N 21/956* | (2006.01) |

(52) U.S. Cl.
CPC ..... *G02B 27/4272* (2013.01); *G03F 7/70633* (2013.01); *G03F 7/70683* (2013.01); *G01N 21/4788* (2013.01); *G01N 21/9501* (2013.01); *G01N 21/956* (2013.01); *G01N 2201/068* (2013.01)

(58) Field of Classification Search
CPC ............ G02B 27/4272; G02B 27/4255; G01B 11/272; G03F 7/70683; G03F 7/70633
See application file for complete search history.

(56) References Cited

U.S. PATENT DOCUMENTS

| | | | |
|---|---|---|---|
| 5,340,992 A * | 8/1994 | Matsugu | G03F 9/7076 250/548 |
| 5,465,148 A * | 11/1995 | Matsumoto | G03F 7/70633 356/490 |
| 6,013,355 A * | 1/2000 | Chen | B32B 7/02 428/209 |
| 6,628,390 B1 | 9/2003 | Johnson | |
| 6,982,793 B1 * | 1/2006 | Yang | G03F 7/70633 356/401 |
| 6,992,764 B1 * | 1/2006 | Yang | B23K 26/04 356/369 |
| 7,046,361 B1 * | 5/2006 | Yang | G03F 7/70633 356/401 |
| 7,242,477 B2 * | 7/2007 | Mieher | G01N 21/956 356/401 |
| 7,289,214 B1 * | 10/2007 | Li | G03F 7/70633 356/401 |
| 7,561,282 B1 * | 7/2009 | Widmann | G03F 7/70625 356/401 |
| 7,671,990 B1 * | 3/2010 | Adel | G03F 7/70633 356/400 |
| 7,834,997 B2 * | 11/2010 | Nakayama | H01J 37/20 250/252.1 |
| 8,189,202 B2 | 5/2012 | Liesener et al. | |
| 8,250,497 B2 | 8/2012 | Hsu et al. | |
| 8,582,114 B2 | 11/2013 | Manassen et al. | |
| 8,854,632 B2 * | 10/2014 | Shibazaki | G03F 9/7003 356/620 |
| 8,908,145 B2 * | 12/2014 | Shibazaki | G03F 7/70641 355/53 |
| 9,046,792 B2 | 6/2015 | Hetzler et al. | |
| 9,134,256 B2 * | 9/2015 | Smilde | G03F 7/70633 |
| 9,257,351 B2 * | 2/2016 | Ausschnitt | H01L 22/12 |
| 9,442,393 B2 | 9/2016 | Hetzler et al. | |
| 9,784,690 B2 * | 10/2017 | Sapiens | G01N 21/9501 |
| 9,811,003 B2 * | 11/2017 | Jak | G03F 7/70625 |
| 9,835,956 B2 * | 12/2017 | Liu | G03F 7/70633 |
| 9,885,961 B1 * | 2/2018 | Amir | G01B 11/14 |
| 9,903,823 B2 * | 2/2018 | Lu | G01B 11/272 |
| 9,910,366 B2 * | 3/2018 | Middlebrooks | G03F 7/70633 |
| 10,061,212 B2 * | 8/2018 | Van Der Schaar | G03F 7/70633 |
| 10,078,268 B2 * | 9/2018 | Den Boef | G01N 21/4788 |
| 10,162,271 B2 * | 12/2018 | Smilde | G03F 7/70625 |
| 10,162,272 B2 * | 12/2018 | Jak | G03F 7/7065 |
| 10,222,709 B2 * | 3/2019 | Quintanilha | G03F 7/70591 |
| 2003/0021465 A1 * | 1/2003 | Adel | G03F 7/70633 382/151 |
| 2004/0264903 A1 * | 12/2004 | Dridi | B82Y 20/00 385/129 |
| 2005/0012928 A1 | 1/2005 | Sezginer et al. | |
| 2005/0122506 A1 | 6/2005 | Wegmann et al. | |
| 2005/0189502 A1 * | 9/2005 | Van Bilsen | G03F 9/7046 250/559.3 |
| 2005/0195398 A1 * | 9/2005 | Adel | B82Y 10/00 356/401 |
| 2005/0208685 A1 * | 9/2005 | Abdulhalim | G03F 7/70633 438/14 |
| 2008/0062432 A1 | 3/2008 | Sandig et al. | |
| 2009/0262362 A1 | 10/2009 | de Groot et al. | |
| 2009/0296075 A1 | 12/2009 | Hu et al. | |
| 2009/0313589 A1 | 12/2009 | Hsu et al. | |
| 2010/0214550 A1 * | 8/2010 | Hulsebos | G03B 27/42 355/74 |
| 2010/0244333 A1 * | 9/2010 | Bedal | B33Y 10/00 264/497 |
| 2011/0032535 A1 * | 2/2011 | Liesener | G03F 7/70633 356/511 |
| 2011/0080585 A1 * | 4/2011 | Rabello | G01N 21/211 356/368 |
| 2012/0033215 A1 | 2/2012 | Kandel et al. | |
| 2012/0044470 A1 * | 2/2012 | Smilde | G03F 1/44 355/53 |
| 2012/0212749 A1 * | 8/2012 | Den Boef | G02B 21/0048 356/615 |
| 2012/0243004 A1 | 9/2012 | El Gawhary et al. | |
| 2013/0010306 A1 | 1/2013 | Coene et al. | |
| 2013/0066597 A1 * | 3/2013 | Van Beurden | G01N 21/4788 703/1 |
| 2013/0278942 A1 | 10/2013 | Jeong et al. | |
| 2013/0293890 A1 * | 11/2013 | Amir | G01B 11/14 356/401 |
| 2015/0177135 A1 * | 6/2015 | Amit | G01N 21/47 702/150 |
| 2016/0291481 A1 | 10/2016 | Smilde et al. | |

* cited by examiner

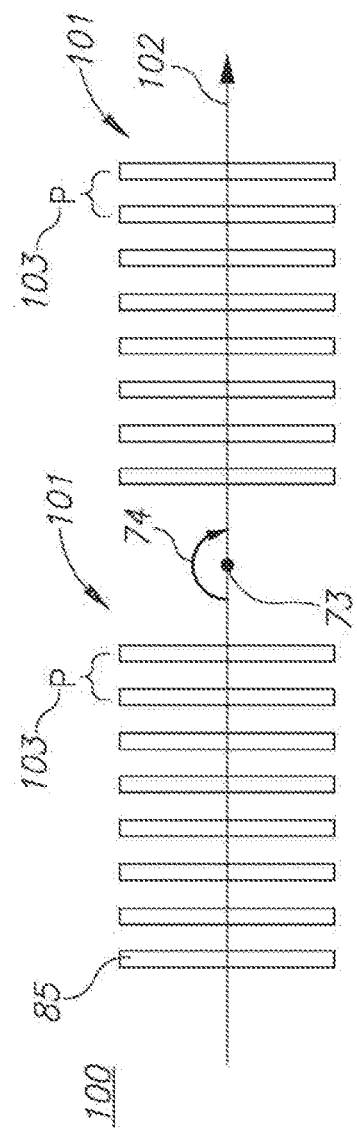
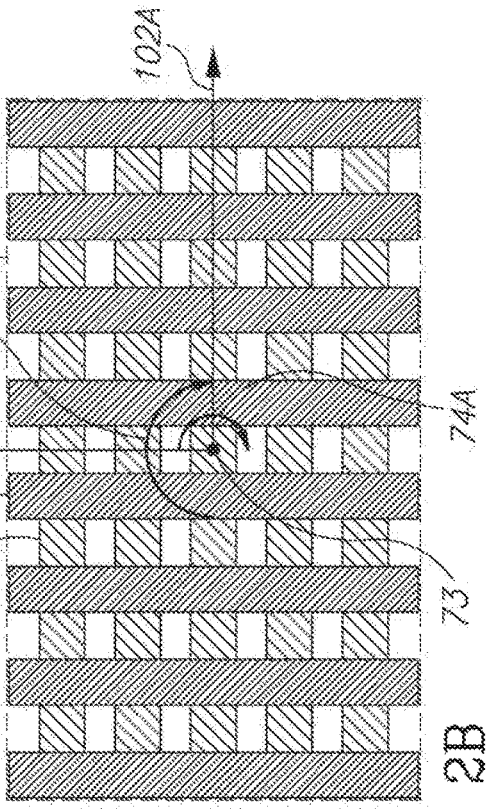
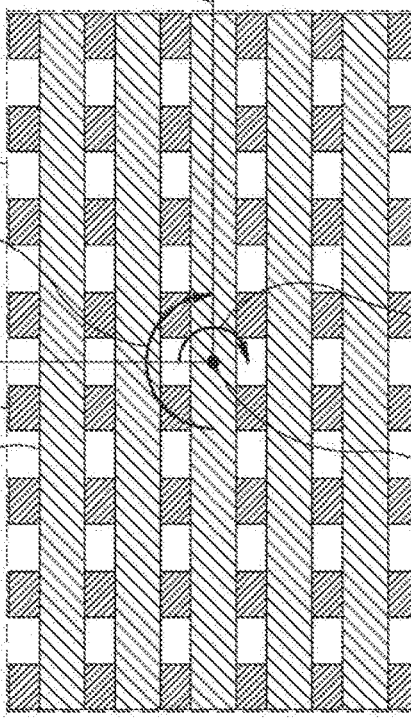
Figure 2A
Figure 2B

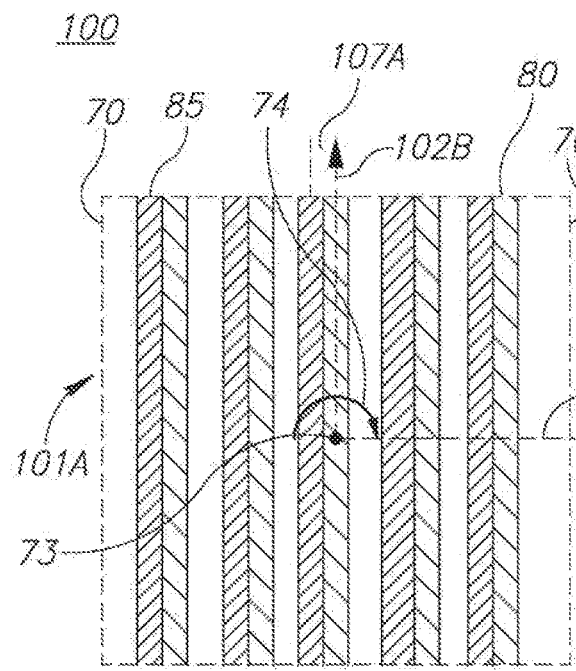 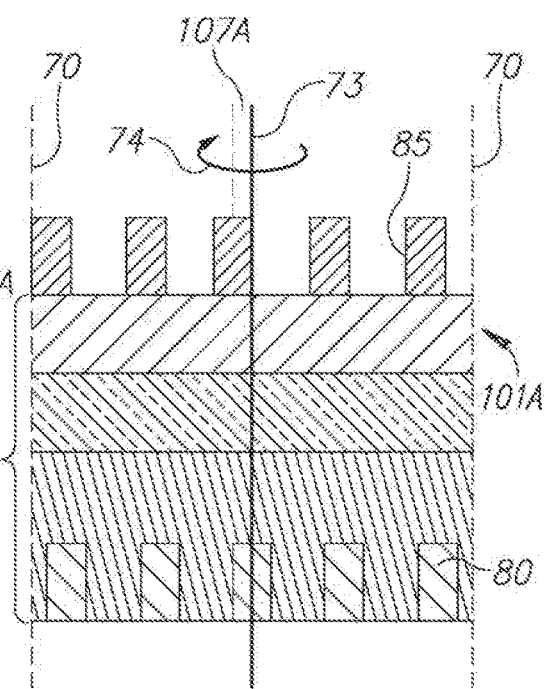
Figure 3A    Figure 3B
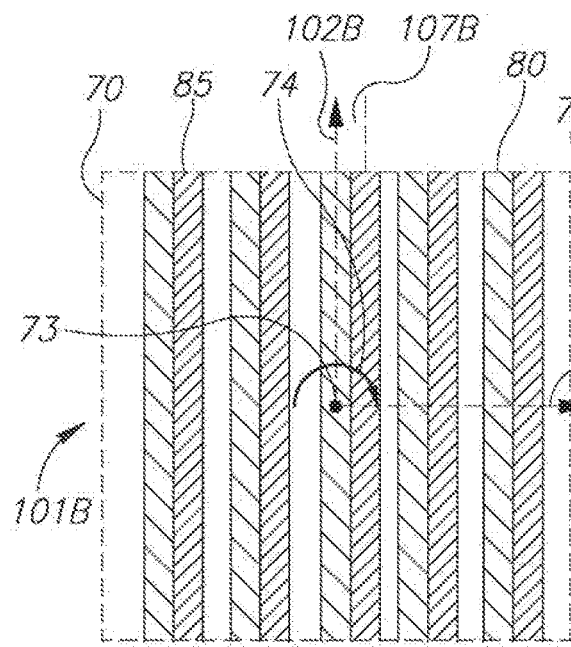 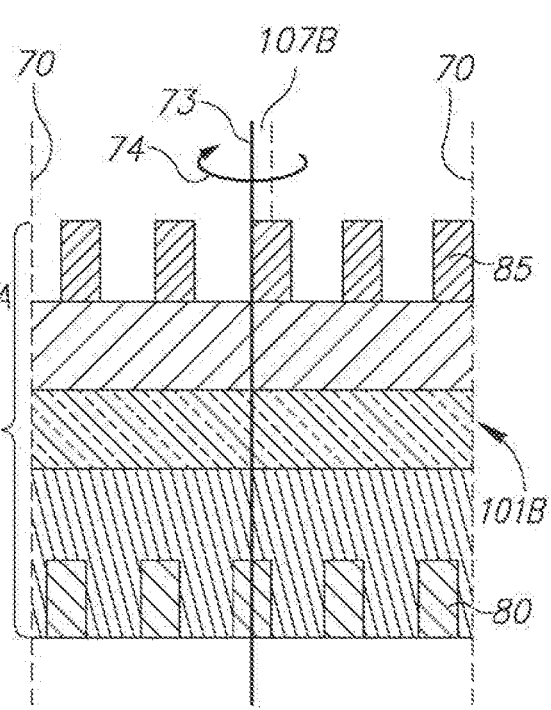
Figure 3C    Figure 3D

200

210 — DESIGNING AND/OR PRODUCING A ROTATIONALLY SYMMETRIC METROLOGY TARGET CELL WITH REFERENCE TO THE CELL EDGES

212 — DESIGNING AND/OR PRODUCING A METROLOGY TARGET CELL TO BE ROTATIONALLY SYMMETRIC WITH RESPECT TO ONE GRATING AND HAVE ANOTHER GRATING OFFSET THEREFROM

214 — DESIGNING AND/OR PRODUCING A METROLOGY TARGET CELL HAVING SOME OF ITS FEATURES ROTATIONALLY SYMMETRIC WITH RESPECT TO THE CELL EDGES

215 — DESIGNING AND/OR PRODUCING A METROLOGY TARGET HAVING MULTIPLE CELLS WITH ELEMENTS THAT ARE INVARIANT UNDER A SPECIFIC TRANSFORM WITH RESPECT TO THE CORRESPONDING CELL BOUNDARIES

218 — DESIGNING AND/OR PRODUCING METROLOGY TARGET CELLS WHICH ARE INVARIANT TO A 180° ROTATION WITH RESPECT TO AT LEAST SOME OF THEIR FEATURES (E.G. ONE GRATING)

220 — USING SYMMETRIC OR PARTIALLY SYMMETRIC TARGET CELLS FOR OVERLAY MEASUREMENTS

225 — REDUCING AN ERROR IN OVERLAY MEASUREMENTS BY USING AT LEAST PARTIALLY ROTATIONAL SYMMETRIC TARGET CELLS

Figure 4

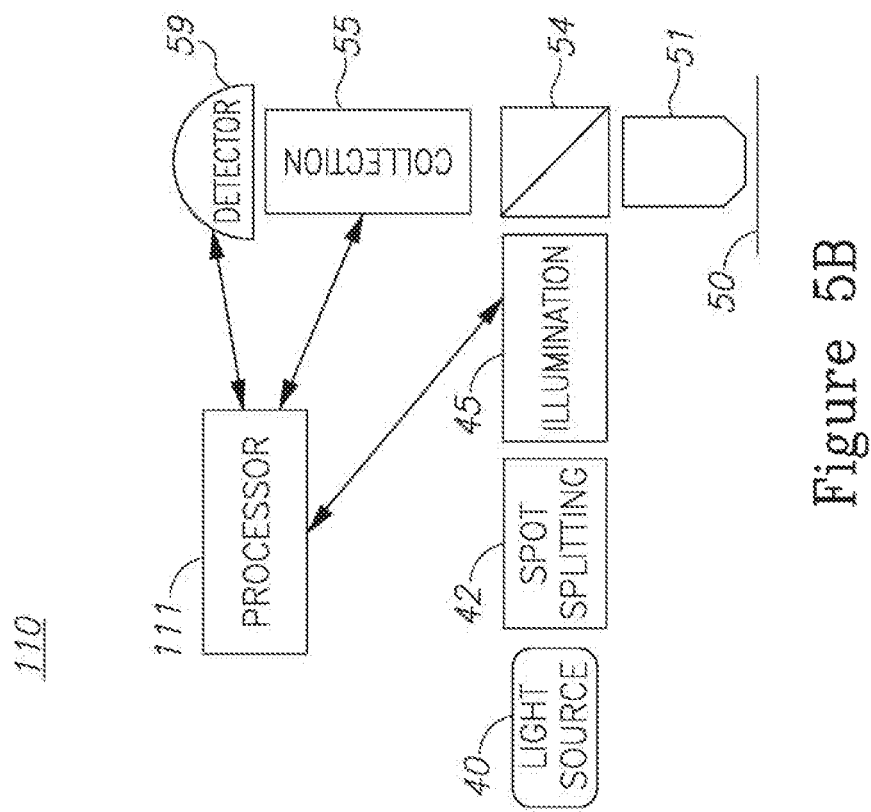
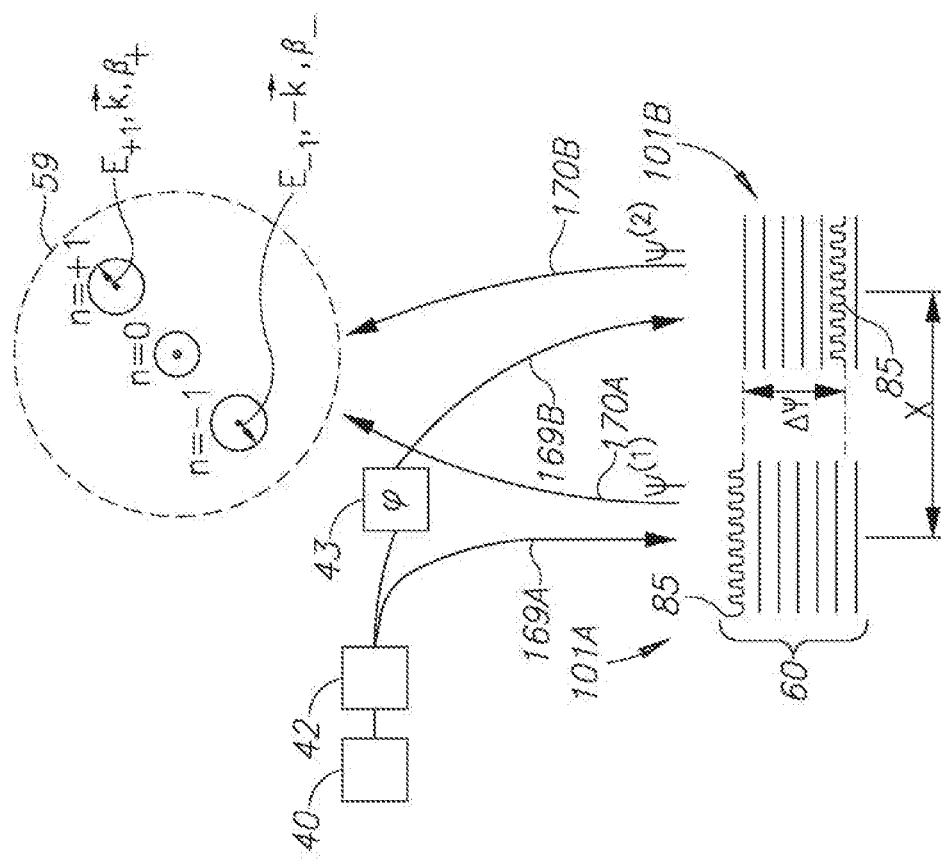
Figure 5B
Figure 5A

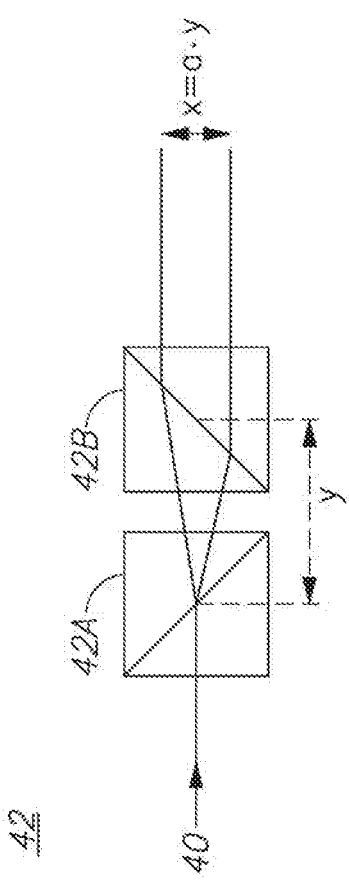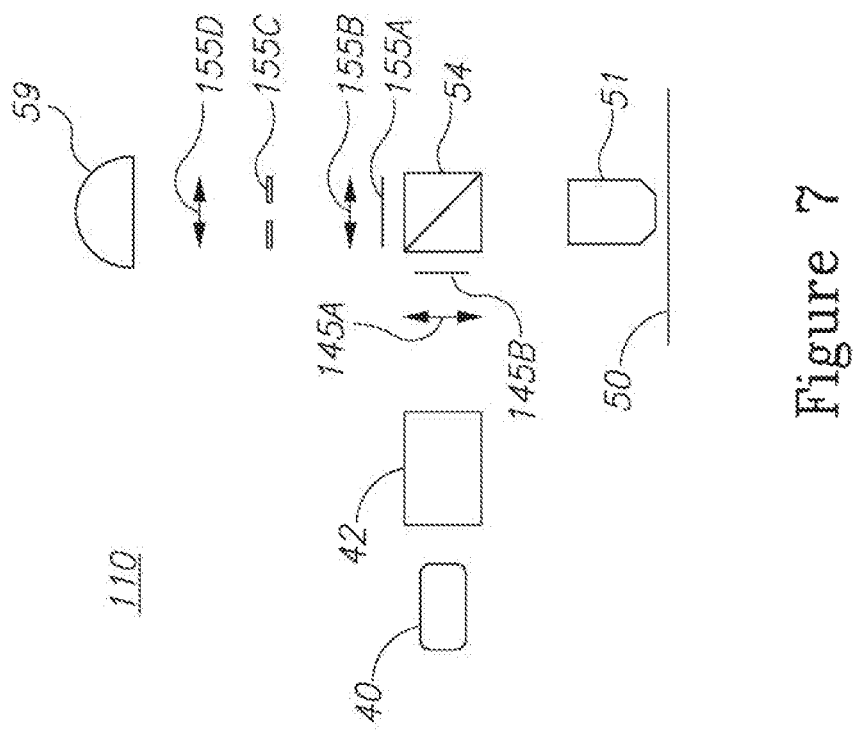

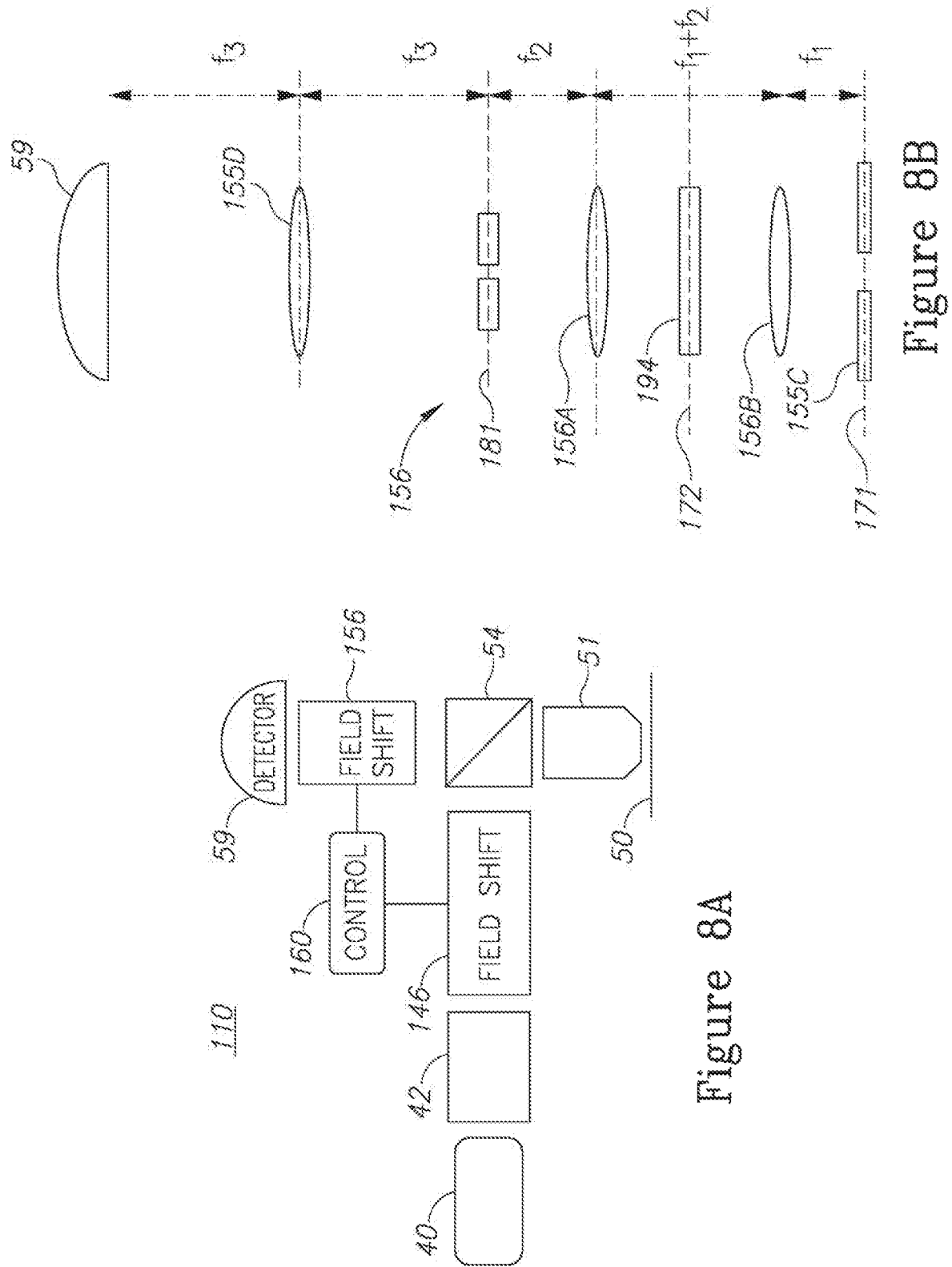

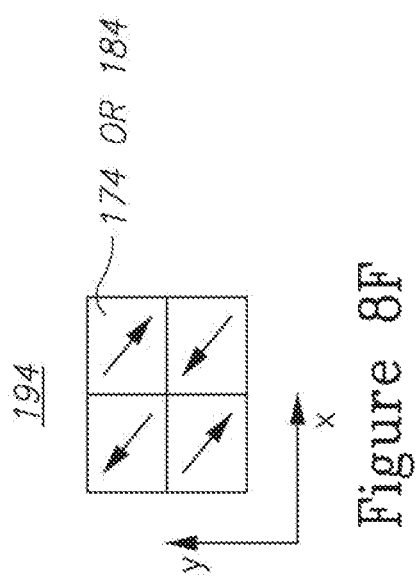
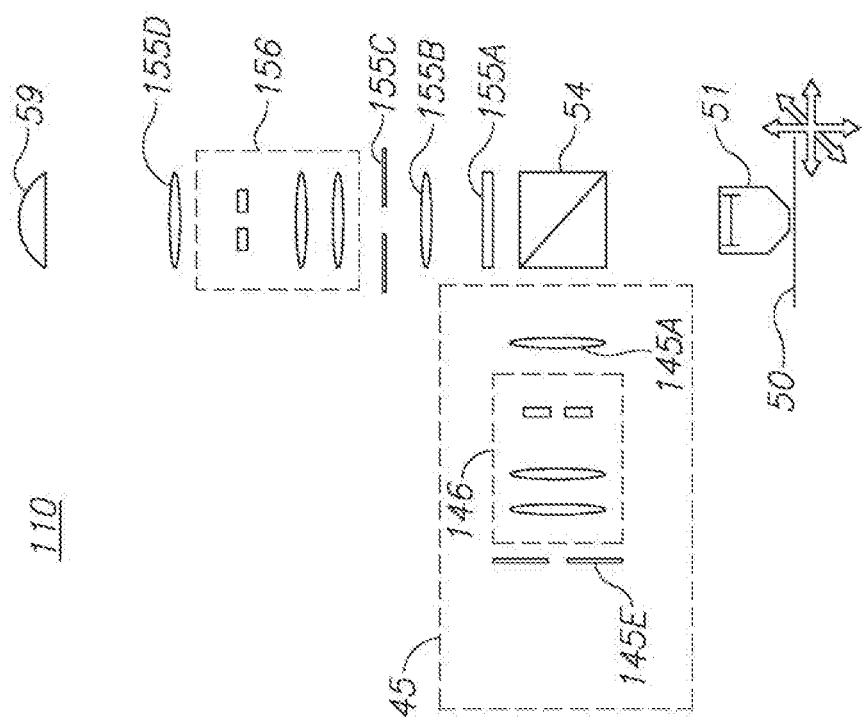
Figure 8F
Figure 8E

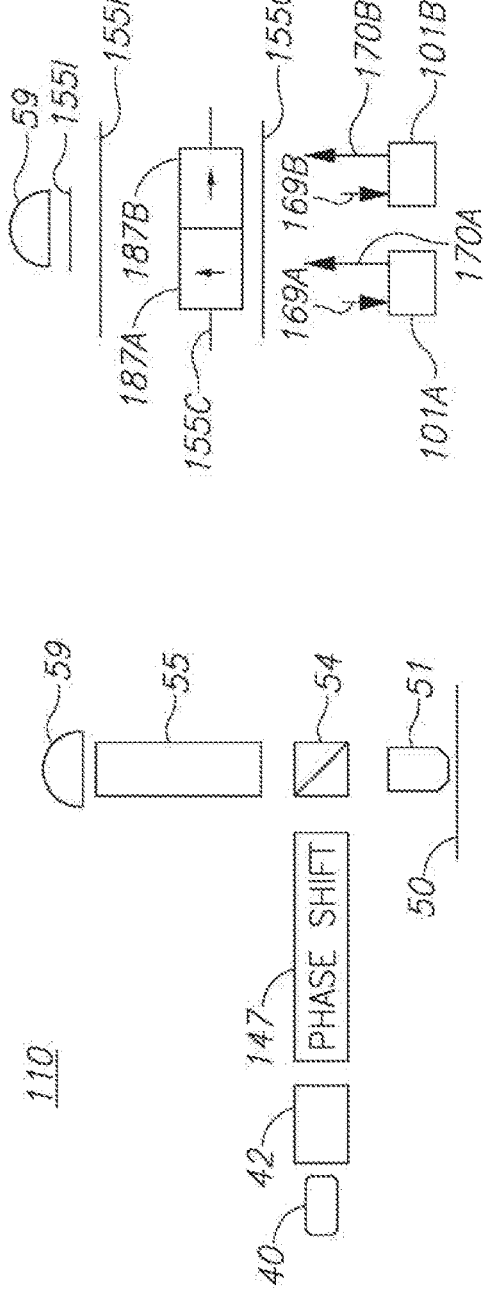
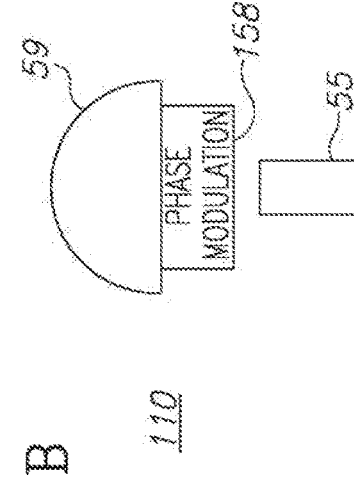
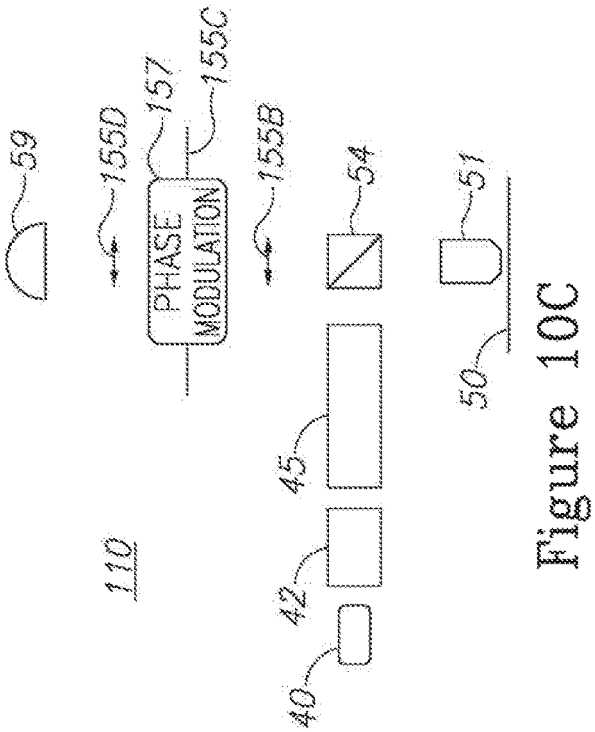
Figure 10A  
Figure 10B  
Figure 10C  
Figure 10D

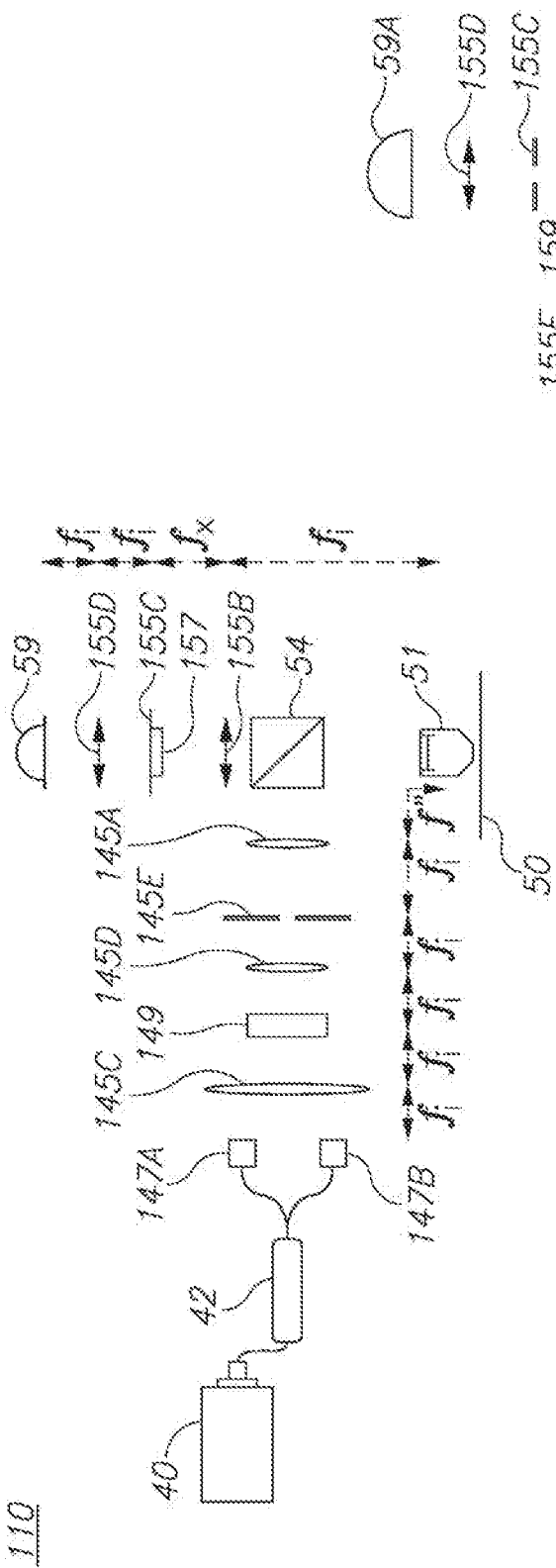
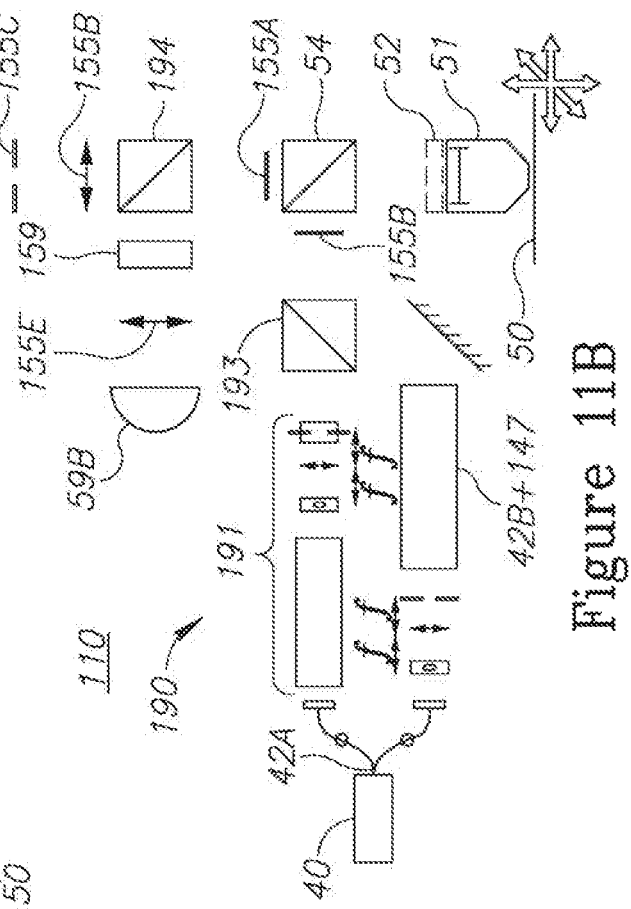
Figure 11A
Figure 11B

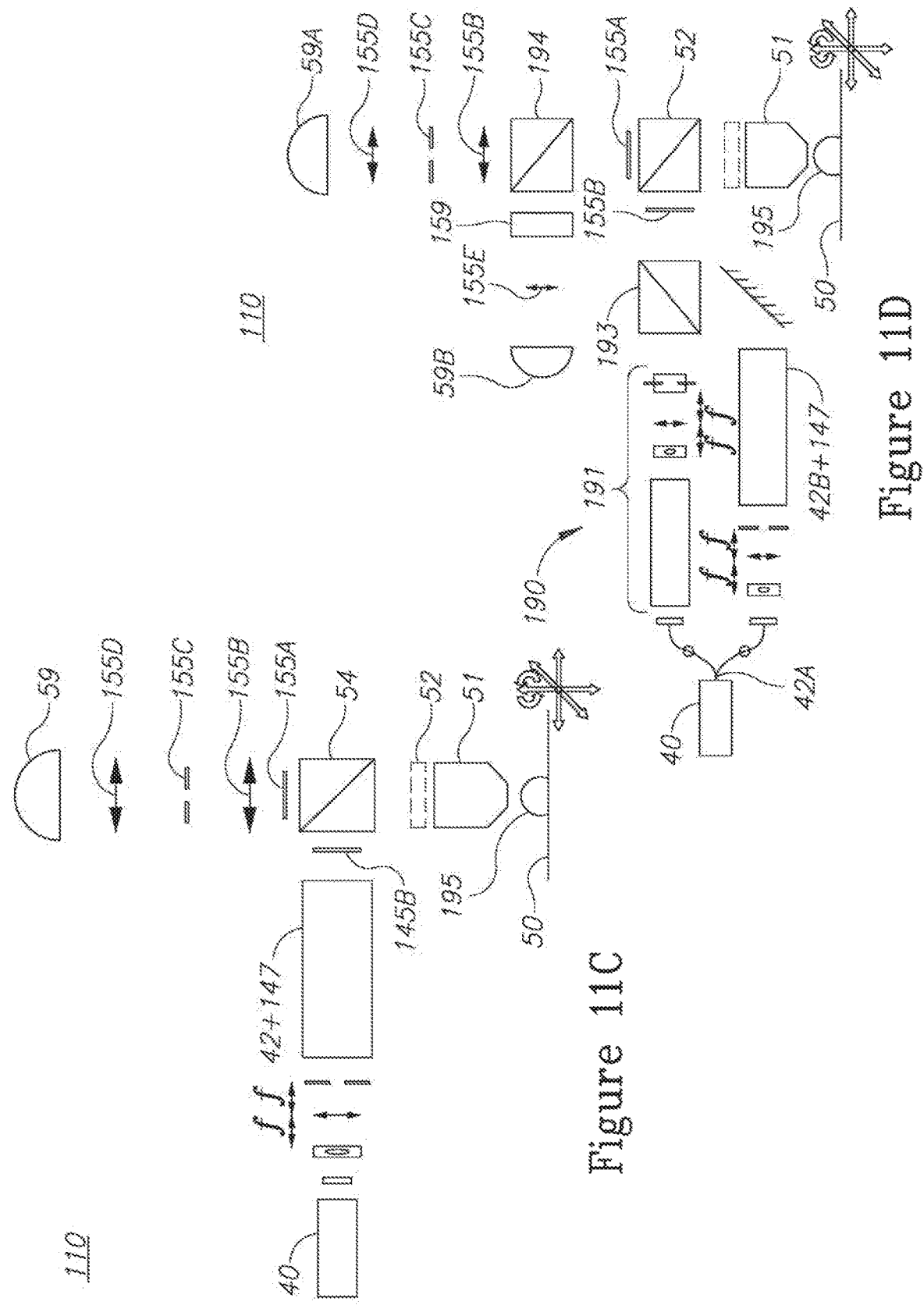

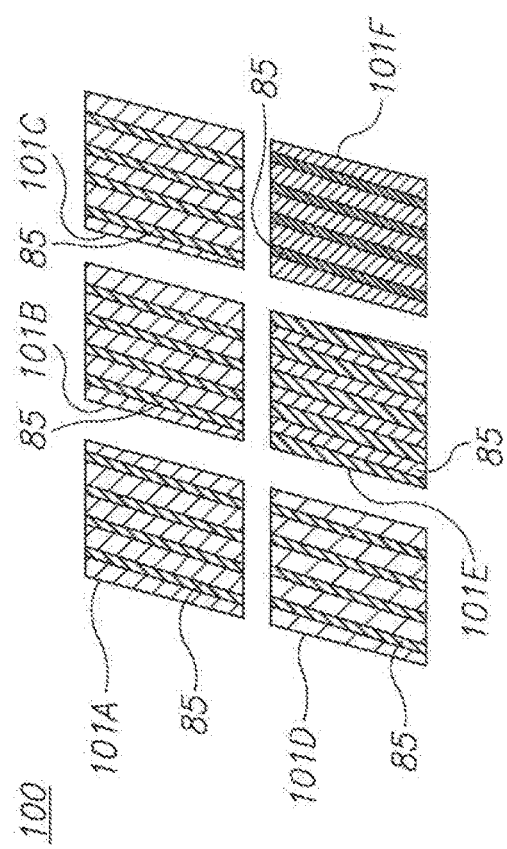
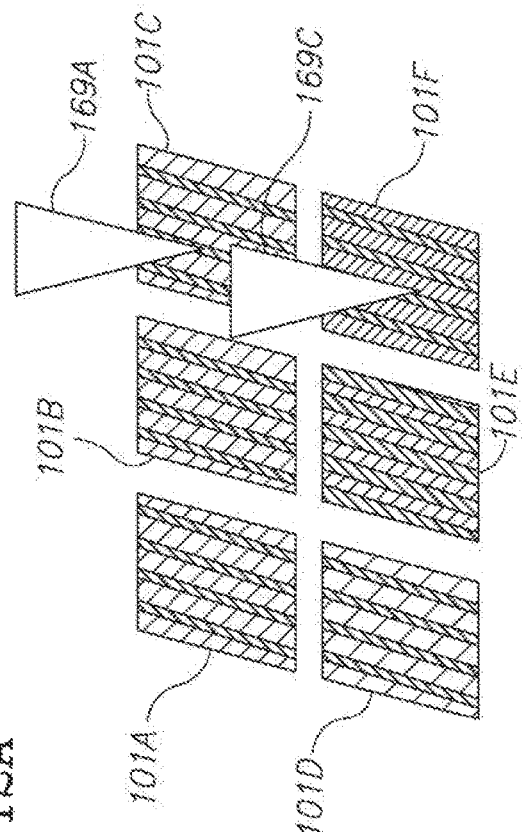
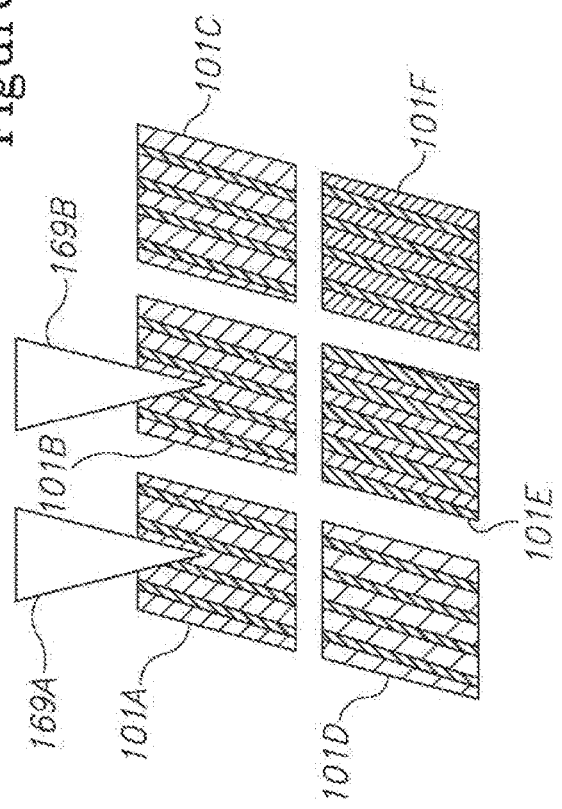
Figure 12A
Figure 12B
Figure 12C

500

- 450 — ILLUMINATING A METROLOGY TARGET THAT COMPRISES AT LEAST TWO PERIODIC STRUCTURES SIDE BY SIDE
- 457 — CONFIGURING THE METROLOGY TARGET TO SATISFY THE RELATION $\psi_n^{(a)}(\vec{k}) = \psi_{-n}^{(a)}(-\vec{k})$
- 460 — INTRODUCING A CONTROLLED VARIABLE THAT EFFECTS THE ILLUMINATION AND/OR COLLECTION BEAMS FROM AT LEAST ONE OF THE PERIODIC STRUCTURES
- 465 — CARRYING OUT THE ILLUMINATION SIMULTANEOUSLY WITH RESPECT TO THE PERIODIC STRUCTURES
- 470 — MEASURING INTERFERENCE OF AT LEAST ONE DIFFRACTION ORDER FROM THE PERIODIC STRUCTURES
- 480 — EXTRACTING THE OVERLAY ERROR FROM THE MEASURED INTERFERENCE
- 485 — EXTRACTING THE OVERLAY ERROR FROM THE MEASURED INTERFERENCE WITH RESPECT TO THE INTRODUCED CONTROLLED VARIABLE
- 490 — ESTIMATING AN OVERLAY ERROR BETWEEN AT LEAST TWO LAYERS WITH THE PERIODIC STRUCTURES

Figure 13

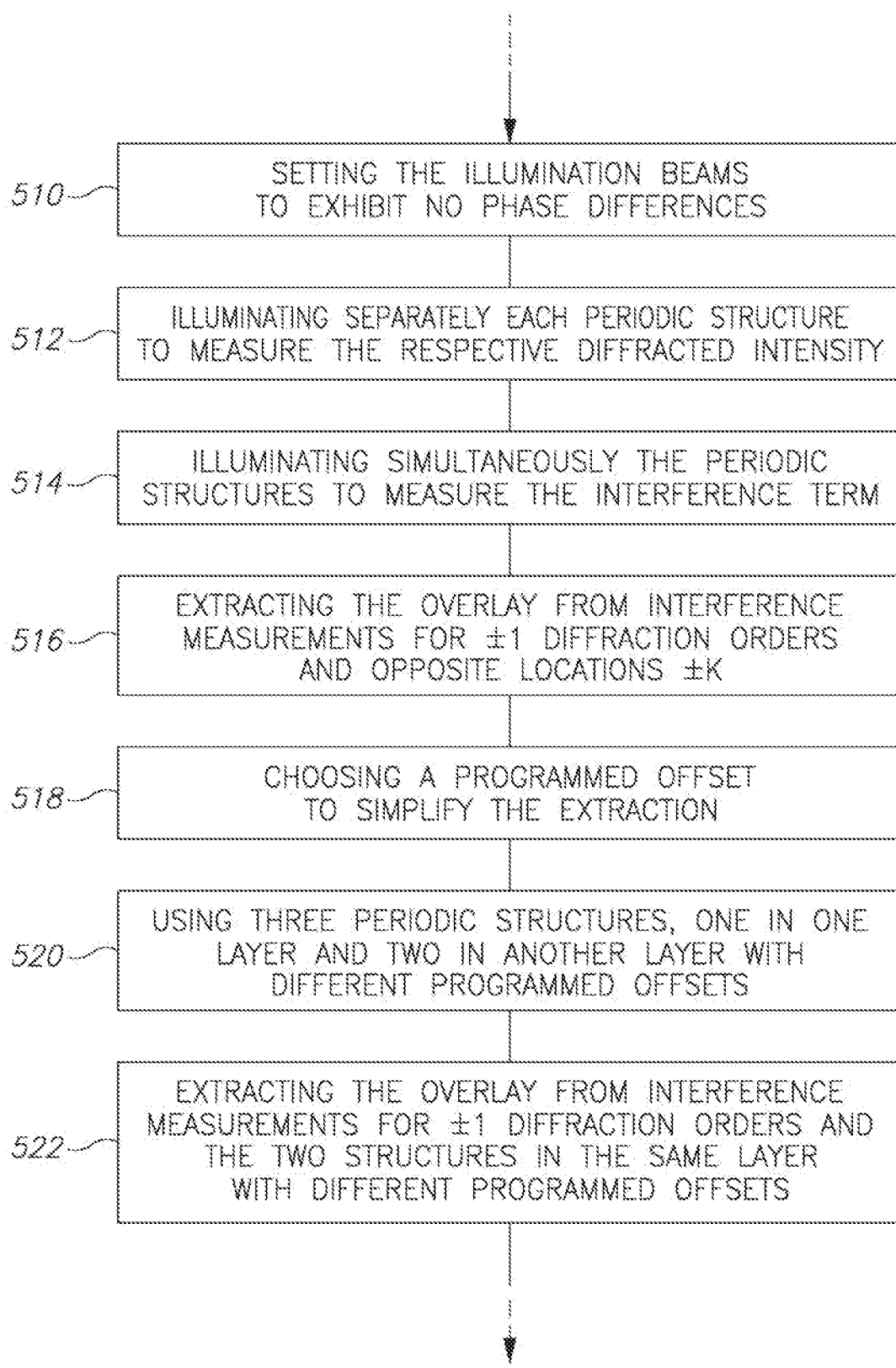
Figure 13 (cont. 1)

*500*

- 524 — TAKING MULTIPLE MEASUREMENTS WITH DIFFERENT ILLUMINATION INTENSITIES
- 526 — EXTRACTING THE OVERLAY FROM INTERFERENCE MEASUREMENTS FOR ±1 DIFFRACTION ORDERS AND THE DIFFERENT ILLUMINATION INTENSITIES
- 528 — TAKING ONE OR MORE MEASUREMENTS WITH A NONZERO COMPENSATED FIELD SHIFT
- 529 — TAKING ADDITIONAL MEASUREMENT(S) WITH A NONZERO PHASE SHIFT
- 530 — IMAGING THE WAFER TO A FIELD CONJUGATE PLANE
- 532 — PERFORMING IMAGE SHIFTING AT THE FIELD CONJUGATE PLANE
- 534 — COMPENSATING FOR THE IMAGE SHIFTING IN THE ILLUMINATION
- 536 — EXTRACTING THE OVERLAY ALGORITHMICALLY FROM THE COMPENSATED IMAGE SHIFTS

Figure 13 (cont. 2)

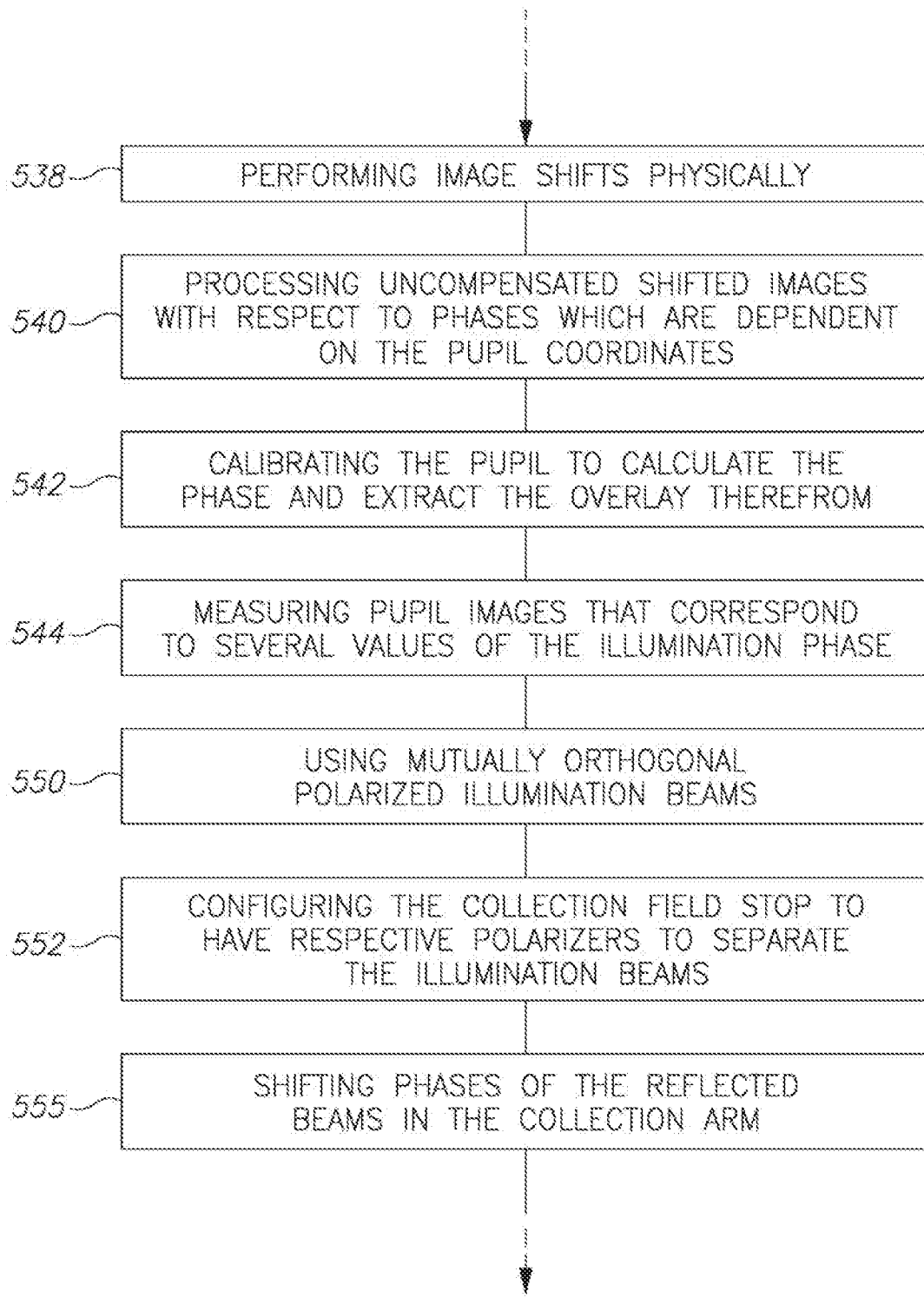
Figure 13 (cont. 3)

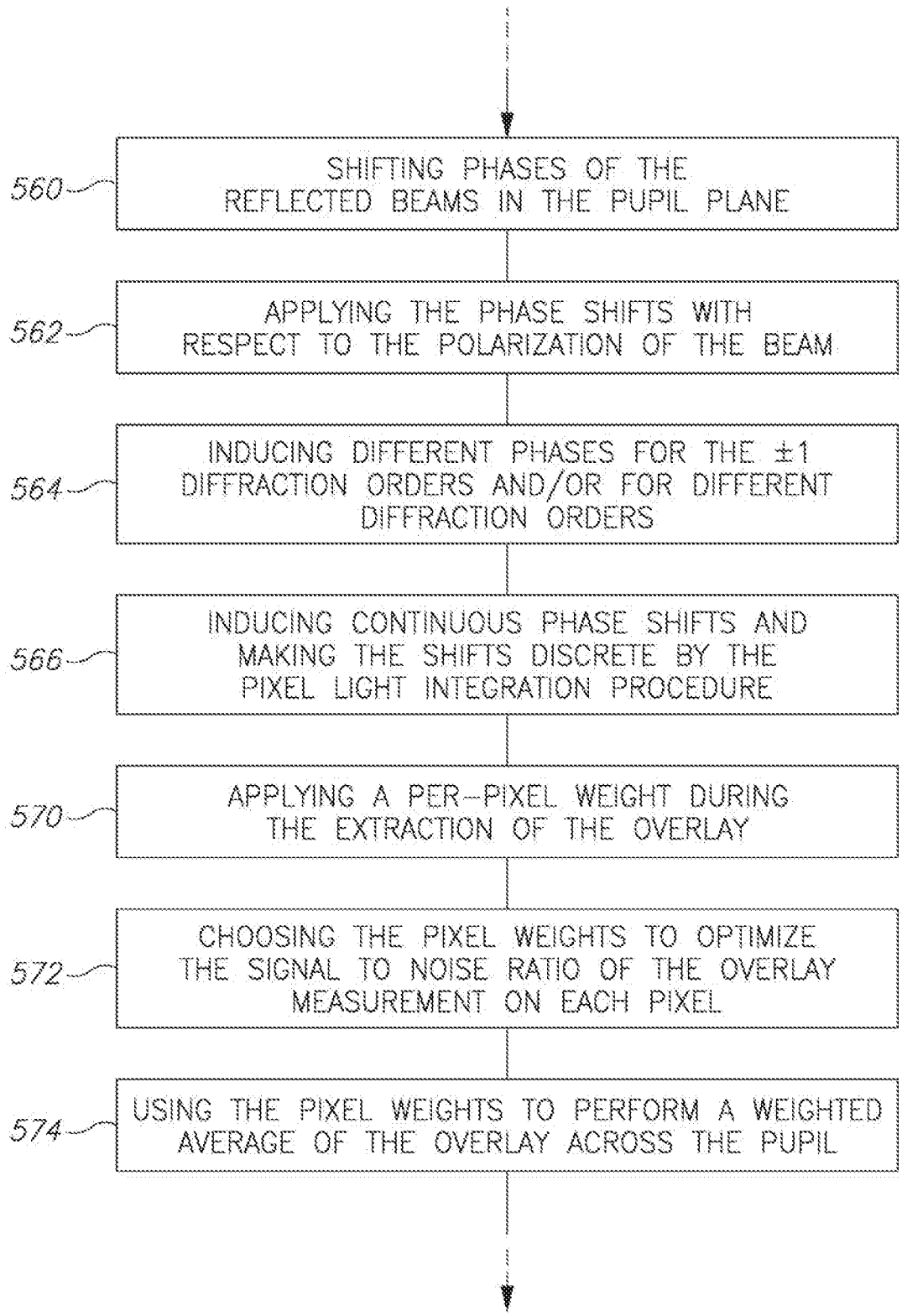
Figure 13 (cont. 4)

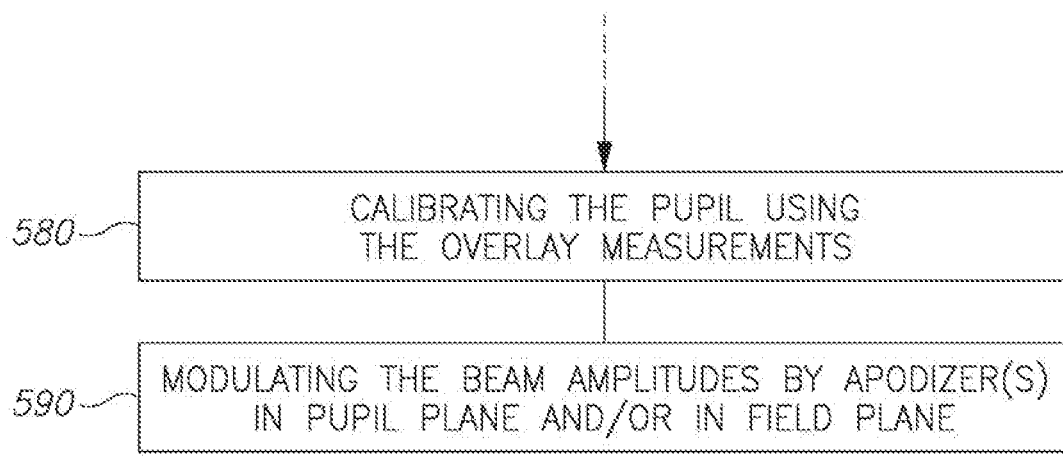
Figure 13 (cont. 5)

SYMMETRIC TARGET DESIGN IN SCATTEROMETRY OVERLAY METROLOGY

CROSS-REFERENCE TO RELATED APPLICATIONS

This application is a divisional patent application filed under 35 USC §§ 120 and 121 based on U.S. patent application Ser. No. 14/161,398, filed on Jan. 22, 2014, which application is a Continuation of International Patent Application Serial No. PCT/US2013/065527, filed on Oct. 17, 2013, which application claims priority of U.S. Provisional Patent Application No. 61/715,603, filed on Oct. 18, 2012 and U.S. Provisional Patent Application No. 61/745,981, filed on Dec. 26, 2012, all of which applications are incorporated herein by reference.

FIELD OF THE INVENTION

The present invention relates to the field of metrology in semiconductor devices, and more particularly, to target design and measurement concepts applicable, among others, to overlay metrology.

BACKGROUND OF THE INVENTION

Periodic scatterometry targets are used to obtain accurate measurements of target features. Such targets include massive arrays of uniformly constructed and uniformly spaced periodic features arranged to provide the best possible targeting information. For example, periodic gratings may be used as targets as may other periodically configured higher dimensional target arrays having uniformly spaced and sized metrology features.

Current scatterometry overlay (SCOL) targets are non-design-rule targets, which include features or spaces as large as 400 nm. A typical SCOL target consists of several cells, each consisting of two gratings (one in each of the layers between which the overlay needs to be measured). An example of a grating in one of these layers is seen in FIG. 1A. In this grating the typical size of a feature or a space is hundreds of nanometers (pitch 103), in contrast with design rule features, which are tens of nanometers in size. The features of a SCOL target are sometimes segmented for better process compatibility as seen in FIG. 1B. The fine pitch 103B of the segmentation can be as small as tens of nanometers, similarly to the design rule of the device. However, the spaces in such a segmented target are still of size of hundreds of nanometers (pitch 103A), and therefore this target may become distorted and noisy because of process effects. This may require spatial averaging of the target, which by itself limits the target size from below to be the spatial averaging size. Furthermore, it is well known that 1st order SCOL technologies tend to be sensitive to asymmetric grating imperfections, and that, in cases where one of the gratings reflects significantly more light than the other, the sensitivity to overlay is low. Finally, to gain more sensitivity to overlay, current SCOL technologies require the printing of more targets on the wafer (with varied programmed offsets). This increases the real-estate of the targets and the COO (cost of ownership) of the metrology tool.

Another aspect of current 1st order SCOL technologies is that they have TIS (tool induced shift) and TIS3s (tool induced shift 3-sigma—a variability value relating to the TIS) that result from non-zero illumination asymmetry. To reduce TIS and TIS3s one needs a variety of error-prone calibration techniques which lead to a residual TIS and TIS3s. Another disadvantage of current 1st order SCOL technologies is that there is no direct per-pupil-coordinate weight that is strongly correlated to accuracy.

Another aspect of current 1st order SCOL technologies is that they are based on comparing signals performed at different times (signals that correspond to pupil images of different target cells). These signals experience different system noise which needs to be removed. The sensitivity of the overlay to miss-handling the system noise is significant, and leads to very tight tolerances on this parameter.

Periodic targeting structures typically feature two layers of similarly oriented periodic gratings formed one over the other. Typically, the layers are designed with a specified predetermined offset with respect to each other. This enables scattering signals to be generated when illuminated by a light beam. A comparison of the actual signal produced with the expected scattering signal enables highly accurate overlay metrology measurements to be made. Optical metrology targets can also comprise of single gratings and/or gratings in a single layer, for example in optical metrology of critical dimension or in overlay optical metrology having targets positioned side by side.

Current SCOL target designs comprise of finite size cells 90 which include gratings 80, 85 of a defined pitch. The number of gratings and their position depends on the specific SCOL technology. For example, in 0th or 1st order SCOL, a target comprises of several cells, each cell comprising of two gratings in two different layers. In the single patterning case, for instance, the two layers are positioned on top of each other, with, possibly, several film layers in between. Relative offset 75 of the grating position includes a programmed offset (pof) and the overlay (ovl). The main SCOL paradigm is that the asymmetry in the cell is solely due to the total offset and so that rotating the target by 180° is equivalent to negating the sign of the total offset. This basic assumption leads to a variety of algorithms that take as input the asymmetry signals of various cells with different values for pof, and use it to extract the overlay.

FIGS. 1C-1H schematically illustrate prior art cells in standard scatterometry overly targets and their deficiencies. FIGS. 1C, 1E and 1G are top views, FIGS. 1D, 1F and 1G are cross sectional views. FIGS. 1C and 1D illustrate a target 90 having one cell with edges 70 and a grating 85 upon a layered target area 60. Generally, targets 90 are not symmetrical with respect to a 180° rotation 74 about a central axis 73 perpendicular to the target's face, due to production considerations. As illustrated in a depiction of one cell 90 in FIGS. 1E and 1F, a lower grating 80 is positioned in the bottom layer of a target area 60 and an upper grating 85 is positioned on the top layer of the layered target area 60. A perimeter 70 depicts the cell edges and an axis 73 that is perpendicular to cell 90 and central with respect to cell edges 70 is depicted too. However, prior art cells 90 do not exhibit symmetry for a 180° rotation 74 about central axis 73, mostly for reasons relating to the manufacturing of the targets. FIGS. 1E-1F illustrate targets having a total offset 75 that is introduced as the sum of difference of a programmed offset (pof) and the overlay (ovl). FIGS. 1G and 1H illustrate a zero offset 75 case. In the top view the pictorial representation shows only the upper grating since the lower grating is hidden by it (they have the same critical dimension—CD in this pictorial representation). FIG. 2F illustrates a high level schematic top illustration of a prior art cell with a two-dimensional target that is asymmetric with respect to 180° rotations 74A, 74B about axis 73 in both dimensions. Common to all these prior art targets is that the target cells are not symmetric with respect to cell edges 70 when subject to 180° rotations about a central perpendicular axis 73.

Scatterometry overlay (SCOL) technology, as illustrated e.g., in WIPO publication no. WO 2004076963, measures an overlay error between congruent targets in different layers by measuring the interferences of reflected diffraction orders from the targets.

BRIEF SUMMARY OF THE INVENTION

One aspect of the present invention provides a method of estimating an overlay error between at least two layers, the method comprising: illuminating a metrology target that comprises at least two periodic structures which are at different layers, are along a common measurement direction and have a same pitch, wherein the metrology target is symmetric with respect to a 180° rotation about an axis that is perpendicular to the target, and wherein the illumination is carried out simultaneously with respect to the at least two periodic structures; measuring interference of at least one diffraction order from the at least two periodic structures; and extracting the overlay error from the measured interference.

These, additional, and/or other aspects and/or advantages of the present invention are set forth in the detailed description which follows; possibly inferable from the detailed description; and/or learnable by practice of the present invention.

BRIEF DESCRIPTION OF THE DRAWINGS

For a better understanding of embodiments of the invention and to show how the same may be carried into effect, reference will now be made, purely by way of example, to the accompanying drawings in which like numerals designate corresponding elements or sections throughout.

In the accompanying drawings:

FIG. 2A is a high level schematic illustration of a side by side SCOL target measurement of the overlay in the x-direction, according to some embodiments of the invention;

FIG. 2B is a high level schematic illustration of a metrology target having two cells, each with periodic structures in two dimensions, according to some embodiments of the invention;

FIG. 3A is a top view of metrology targets having cells with opposite offsets, according to some embodiments of the invention;

FIG. 3B is a cross sectional view of metrology targets having cells with opposite offsets, according to some embodiments of the invention;

FIG. 3C is a top view of metrology targets having cells with opposite offsets, according to some embodiments of the invention;

FIG. 3D is a cross sectional view of metrology targets having cells with opposite offsets, according to some embodiments of the invention;

FIG. 4 is a high level flowchart illustrating a metrology target design method, according to some embodiments of the invention;

FIG. 5A is a highly schematic illustration of the side by side paradigm, according to some embodiments of the invention;

FIG. 5B is a high level schematic illustration of a metrology system that may be adapted to measure targets in the side by side paradigm, according to some embodiments of the invention;

FIG. 6C is a high level schematic illustration of a beam splitter in the illumination arm of a metrology system, according to some embodiments of the invention;

FIG. 6D is a high level schematic illustration of a beam splitter in the illumination arm of a metrology system, according to some embodiments of the invention;

FIG. 7 is a high level schematic illustration of a metrology system that may be adapted to measure targets in the multiple measurements example, according to some embodiments of the invention;

FIG. 8A is a high level schematic illustration of a metrology system that may be adapted to measure targets in the compensated field shifts example, according to some embodiments of the invention;

FIG. 8B is a high level schematic illustration of a field shifting mechanism in the collection arm, according to some embodiments of the invention;

FIG. 8E is a high level schematic illustration of a metrology system with compensated field shifting, according to some embodiments of the invention;

FIG. 8F is a high level schematic illustration of a two dimensional arrangement of optical elements, according to some embodiments of the invention;

FIG. 10A is a high level schematic illustration of a metrology system that may be adapted to measure targets in the phase shifts example, according to some embodiments of the invention;

FIG. 10B is a high level schematic illustration of a metrology system that may be adapted to measure targets with a polarized collection field stop, according to some embodiments of the invention;

FIG. 10C is a high level schematic illustration of a metrology system that may be adapted to measure targets in the collection phase shifts example, according to some embodiments of the invention;

FIG. 10D is a high level schematic illustration of a metrology system that may be adapted to measure targets in the pupil phase shifts example, according to some embodiments of the invention;

FIG. 11A is a high level schematic illustration of a metrology system that combines spot splitting with optical offsets or phase modulations, according to some embodiments of the invention;

FIG. 11B is a high level schematic illustration of a metrology system that enables alternation between using spot splitting with phase shifting and using a de-coherence system in the illumination arm, according to some embodiments of the invention;

FIG. 11C is a high level schematic illustration of a metrology system that combines spot splitting and phase shifting with near field technologies, according to some embodiments of the invention;

FIG. 11D is a high level schematic illustration of a metrology system that combines spot splitting with phase modulation, de-coherence system and a near field technologies, according to some embodiments of the invention;

FIG. 12A is a high level schematic illustration of metrology targets with multiple cells, according to some embodiments of the invention;

FIG. 12B is a high level schematic illustration of metrology targets with multiple cells, according to some embodiments of the invention;

FIG. 12C is a high level schematic illustration of metrology targets with multiple cells, according to some embodiments of the invention; and FIG. 13 is a high level schematic flowchart illustrating a metrology method, according to some embodiments of the invention.

DETAILED DESCRIPTION OF THE INVENTION

Figure 1A:
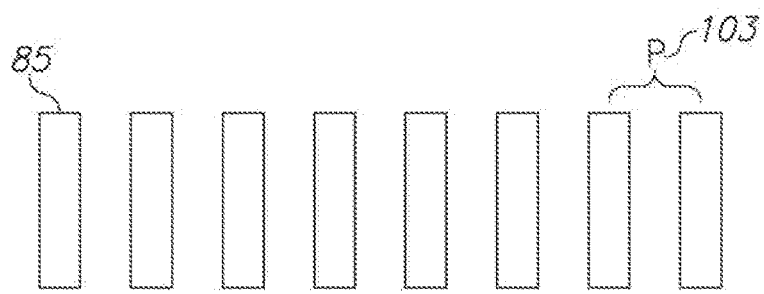
FIG. 1A is a high level schematic illustration of a prior art grating used in a SCOL target.
Figure 1B:
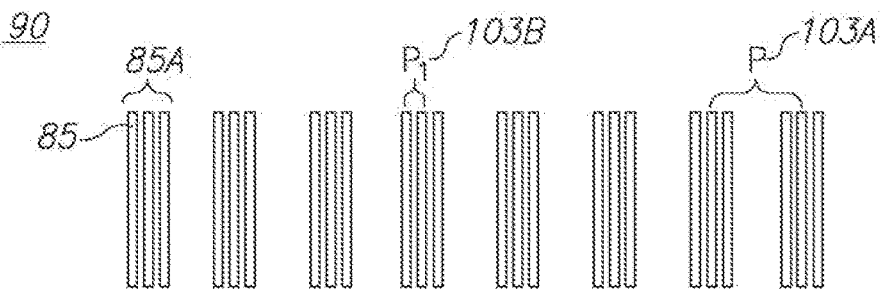
FIG. 1B is a high level schematic illustration of a prior art grating used in a SCOL target showing segmentation of the grating.

Prior to the detailed description being set forth, it may be helpful to set forth definitions of certain terms that will be used hereinafter.

The terms "target" or "metrology target" as used in this application refer to a region from which metrology information is extracted. Metrology targets may be positioned on dedicated areas on the chip, on device edges or within the device area.

The term "periodic structure" as used in this application refers to any kind of designed or produced structure in at least one layer which exhibits some periodicity. The periodicity is characterized by its pitch, namely its spatial frequency. In the present application, periodic structures are occasionally referred to in a non-limiting manner as "grating" as these are simple and common periodic structures that are used for metrology. Such use however is not to be understood as limiting the term "periodic structure" in any way.

The terms "cell" or "grating cell" as used in this application refer to an area which includes at least one periodical structure for metrology measurements. Metrology targets may comprise one or more cell, which comprises periodic structures on one or more layers. Different cells may comprise distinct structures or different areas or parts of a single structure.

The terms "boundaries" or "cell boundaries" as used in this application refer to a circumference of a target cell, determined with respect to characteristics of the target cells. For example, for a single layer target, the boundary may be defined from the properties of that single layer and the target. For example, for grating-on-grating targets the boundary may be defined per layer (per grating) and the symmetric target design dictates that at least one of the boundaries obeys symmetry. The cell boundaries may be a frame that separates the cell from its surrounding, in case such a frame is present. If a frame is not present, the cell boundary may be defined in a non-limiting manner as the perimeter of the smallest area containing the printed structure which can be un-ambiguously associated with the relevant grating or periodic structure. For example, in case of a grating, the boundary may be defined as the perimeter of the smallest area which contains the resist bars in a resist grating.

The term "scatterometry overlay (SCOL)" as used in this application refers to a metrology method that derives metrology information from the phases of diffraction orders (e.g. the +1 and −1 diffraction orders) that reflect off targets which contain periodic structures such as gratings or grating cells.

The term "side by side" as used in this application refers to areas in a metrology targets which are positioned at least partly adjacent to each other and not one beneath the other.

The terms "symmetry" or "rotational symmetry" in relation to targets, as used in this application, refer to a rotational symmetry upon rotating the target 180° about an axis through the center of the target and which is perpendicular to the target.

The term "overlay" as used in this application refers to a non-programmed shift between two layers in a chip. The terms "programmed offset" or "offset" as used in this application refers to a specified intentionally-introduced shift between layers.

With specific reference now to the drawings in detail, it is stressed that the particulars shown are by way of example and for purposes of illustrative discussion of the preferred embodiments of the present invention only, and are presented in the case of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

Before at least one embodiment of the invention is explained in detail, it is to be understood that the invention is not limited in its application to the details of construction and the arrangement of the components set forth in the following description or illustrated in the drawings. The invention is applicable to other embodiments or of being practiced or carried out in various ways. Also, it is to be understood that the phraseology and terminology employed herein is for the purpose of description and should not be regarded as limiting.

Certain embodiments comprise metrology targets 100 having at least two periodic structures 85 which are at different layers 60. Periodic structures 85 (e.g. gratings 85) are along a common measurement direction 102 and have a same pitch 103 and metrology target 100 is symmetric with respect to a 180° rotation 74 about an axis 73 that is perpendicular to target 100. A metrology system 110 is arranged to measure an overlay shift or error in direction 102 between layers 60.

Examples for Targets

Scatterometry overlay (SCOL) derives metrology information from the phases of diffraction orders (e.g. the +1 and −1) that reflect off targets 100 which contain periodic structures 85 such as gratings 85 or grating cells 101. In certain embodiments, periodic structures 85 are located side by side (e.g., at different layers) as illustrated in FIG. 2A. In such embodiments, two cells 101 may be printed on layers 60 between which one wishes to measure the overlay (e.g. the process layer and the resist layer). In a non-limiting example, each cell 101 comprises a single grating 85 as the periodic structure, and both cells 101 are illuminated simultaneously. For example, the simultaneous illumination may be carried out by two coherent light sources, by light split from a single coherent source (e.g. a laser beam), or by light split from a single incoherent source (e.g. a broadband light source). The reflections of the two cells interfere in pupil plane, and this interference contains the overlay information.

FIG. 2A is a high level schematic illustration of a side by side SCOL target 100 measurement of the overlay in the x-direction, according to some embodiments of the invention. FIG. 2A schematically illustrates an example of a side-by-side target 100 for measuring the overlay in direction 102, which is referred to in the following as the x direction. A pitch 103 of both gratings 85 is identical, and for a given pitch 103, the wavelength(s) of illumination are selected to include the relevant diffraction orders (e.g. the first and minus first orders) at least partially within the collection pupil. This allows one to use wavelengths and pitch values in a large range, the former including both the visible and non-visible range. Cells 101 may be placed in arbitrary relative positions on the same wafer site (for example, along the x-axis, as FIG. 2A demonstrates, or along the y-axis, or along the diagonal $$\frac{\hat{x} + \hat{y}}{\sqrt{2}},$$

or along any other axis in the wafer plane). To measure the overlay in the y-direction, additional cells 101 may be used, with periodic structures 85 such as gratings 85 along the y-direction. In a non-limiting example, a two dimensional overlay metrology may be implemented by four side-by-side cells 101 two for the measurement of the x-overlay and two for the measurement of the overlay in the y-direction. In such embodiments, the measurement time may be shortened by using four measurement beams, two falling on the grating cells for the x direction and two falling on the grating cells for the y direction. The beams may be all simultaneous or pairwise simultaneous with respect to measurement directions 102. Each pair of two beams that fall on a pair of cells 101 that are in the same direction 102 are coherent among themselves. All the four beams may or may not be coherent among themselves. The signal from each pair of cells with grating lines in the same direction appears at different portions of the collection pupil, as it happens in the case of targets of the form presented in FIGS. 2A and 2B.

FIG. 2B is a high level schematic illustration of a side by side SCOL target 100 for a simultaneous measurement of the overlay in the x-direction and the y-direction, according to some embodiments of the invention. In a non-limiting example illustrated in FIG. 2B, two cells 101 are used to implement a two dimensional overlay metrology. In the example, cell 101A contains a grating 80A in one direction 102A in the bottom layer and a grating 85A in the orthogonal direction 102B in the upper layer, while cell 101B has gratings 80B, 85B respectively in the same layers, but with opposite directions to those of cell 101A. Such targets 100 allow the simultaneous measurement of the x and y overlays, and reduce the target real-estate by a factor of two.

FIG. 12A-12C are high level schematic illustration of metrology targets 100 with multiple cells, according to some embodiments of the invention. As explained below (after presenting the side by side paradigm and the examples), multiple adjacent target cells 101A-101F may be used to yield many more measurement results per wafer area than SCOL targets which require multi-layered cells.

Certain embodiments of the invention comprise methods for designing and/or producing any of targets 100 illustrated above and below, as well as variations of such targets according to the measurement principles presented below. Certain embodiments comprise sets of design rules as well as wafers that comprise such targets 100.

In certain embodiments, the target's zeroth order reflectivity is reduced with respect to its first order reflectivities, to improve measurement accuracy. The ideal signal in SCOL measurements is coming only from the ±1st orders of the two gratings, without any inaccuracy contributed by leakage of 0th order light into the ±1st orders regions due to diffractions from objects in field planes. However, current 1st order SCOL technologies do not allow reducing the zeroth order reflectivity because, as the signals originate in a grating-over-grating stack, the zeroth and ±1st order signals actually results from all possible combinations of nth order light from the first grating and the mth order light from the second, with n+m=0,±1, respectively. Therefore, the relative reflectivities are not separable by diffraction order. In contrast, the side by side paradigm and targets enable such separation, as the periodic structures do not overlap. Hence, it is possible to design side by side targets and periodic structures are designed to have a lower reflectivity of a zeroth diffraction order than a reflectivity of ±1st diffraction orders.

Rotational Symmetry of Targets

Figure 1C:
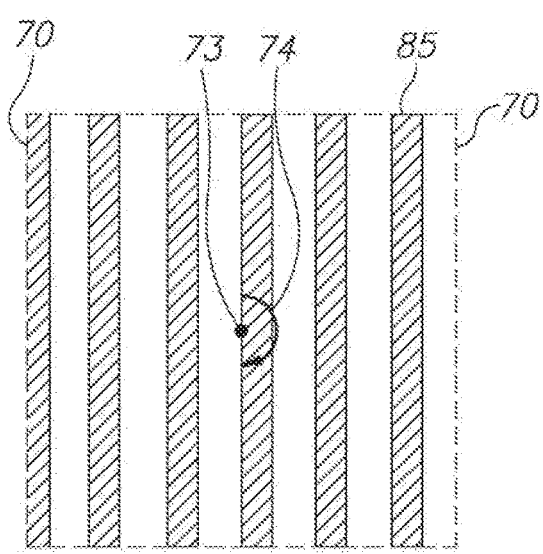
FIG. 1C is a top view of prior art cells in standard scatterometry showing a target having one cell with edges and a grating upon a layered target area.
Figure 1D:
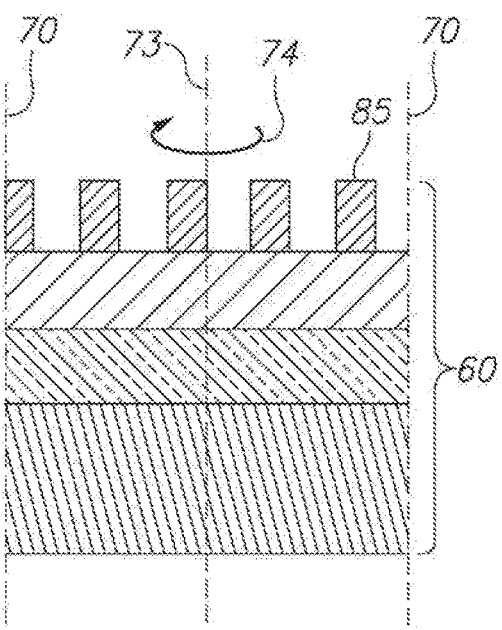
FIG. 1D is a cross sectional view of prior art cells in standard scatterometry showing a target having one cell with edges and a grating upon a layered target area.
Figure 1E:
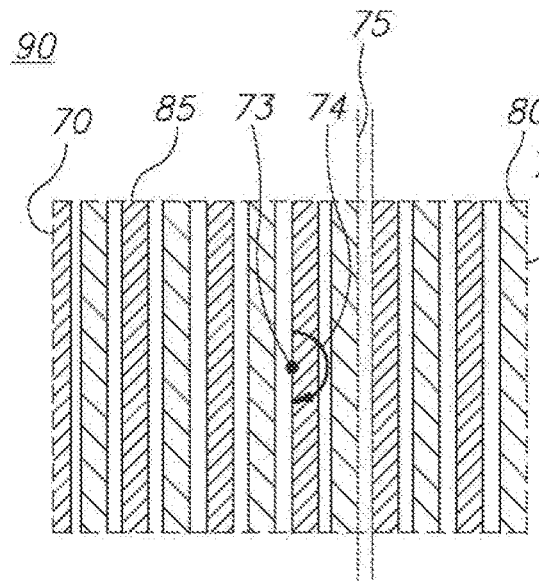
FIG. 1E is a top view of prior art cells in standard scatterometry showing a lower grating positioned in the bottom layer of a target area and an upper grating positioned on the top layer of the layered target area where there is a non-zero total offset.
Figure 1F:
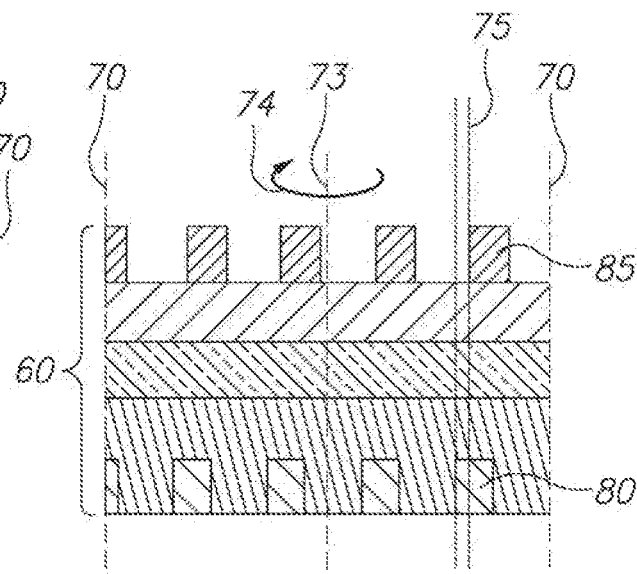
FIG. 1F is a cross sectional view of prior art cells in standard scatterometry showing a lower grating positioned in the bottom layer of a target area and an upper grating positioned on the top layer of the layered target area where there is a non-zero total offset.
Figure 1G:
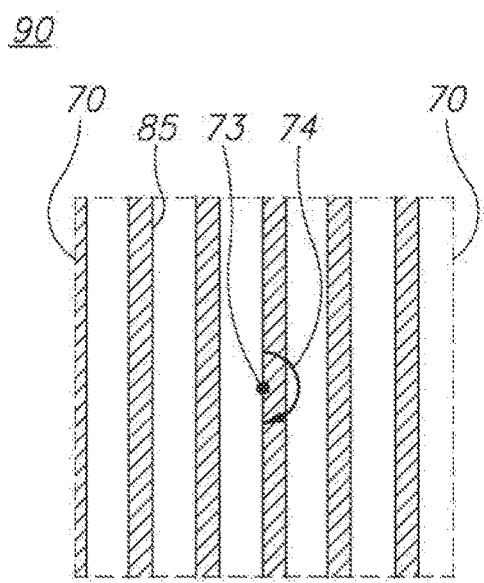
FIG. 1G is a top view of prior art cells in standard scatterometry showing a lower grating positioned in the bottom layer of a target area and an upper grating positioned on the top layer of the layered target area where there is zero total offset.
Figure 1H:
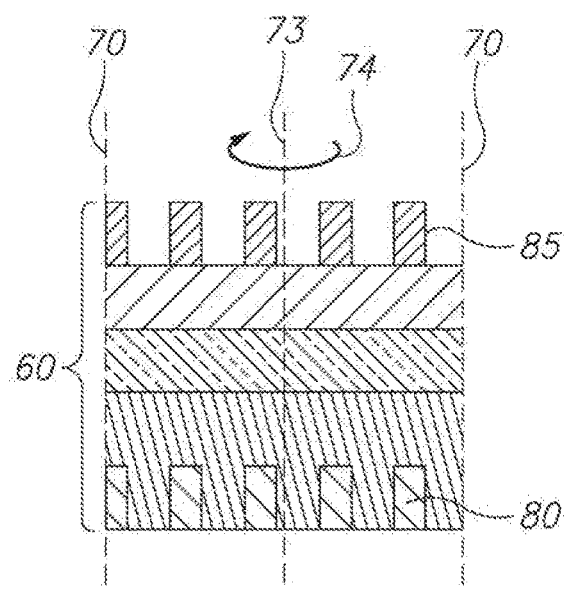
FIG. 1H is a cross sectional view of prior art cells in standard scatterometry showing a lower grating positioned in the bottom layer of a target area and an upper grating positioned on the top layer of the layered target area where there is zero total offset.

The current invention overcomes the following disadvantage of prior art targets, which is illustrated in FIGS. 1E and 1F. The inventors have discovered that this disadvantage relates to the (rotational) symmetry breaking induced by diffraction effects from edges 70 of cell 90. SCOL technologies assume that a 180° rotation of target 90 results in a target having total offset 75 opposite in sign to the original total offset. However, the edge effects can also be a source for a symmetry breakdown and cause a breakdown of this assumption. This is true both in first order SCOL technologies and in zeroth order SCOL technologies. For example, consider the grating-over-grating with a relative zero total offset illustrated in FIGS. 1E and 1F (such a cell will be printed if the overlay is minus the programmed offset).

Since the total induced offset is zero, the assumption mentioned above means that this cell should be symmetric to 180° rotations and so that its signal asymmetry should be zero. But this expectation ignores the symmetry breakdown induced by the finite size effects of the cell's edge. As is clear from FIGS. 1E and 1F, these finite size effects make prior art cell 90 non-invariant to 180° rotation despite its vanishing total offset. This problem exists as long as the cells do not exhibit infinite cell size.

In embodiments, the symmetry operation that is referred to in the disclosure is the 180° rotation with respect to an axis that is perpendicular to the target. This symmetry operation is commonly used with respect to SCOL signals. However, certain embodiments of the invention are not limited to this case, and in cases of other targets and other symmetry operations, embodiments of the invention may comprise designing target cells that are invariant with respect to the cell edges under any specified transform.

The current invention overcomes this neglect of edge-induced asymmetry effects which lead to significant inaccuracy in the overlay measurement that can range from a few to tens of nanometers, depending on the stack, wave length, polarization, and cell size.

As metrology target cells become smaller, the error introduced by edge effects increases. In particular, edge effects may produce an additional offset between gratings at different layers, beyond the designed offset (which is known) and the uncontrollable offset (which is to be measured). Certain embodiments of the invention introduce cells having gratings which are symmetrical with respect to the cell edges defining the cell frame. The symmetry cancels out edge effects. Target cells may be either fully symmetrical by design, or targets may include complementary cells having opposite designed offsets.

Figure 2C:
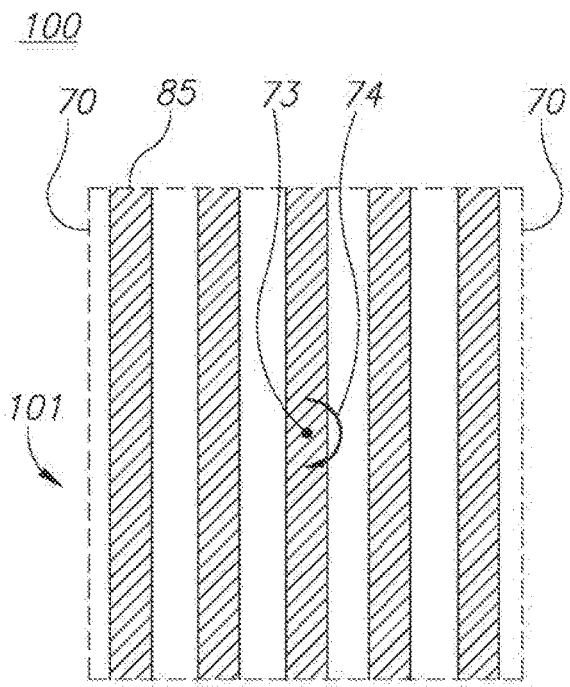
FIG. 2C is high level schematic top view illustration of metrology targets having zero offset with periodic structures in one layer or congruent periodic structures in two layers, according to some embodiments of the invention.
Figure 2D:
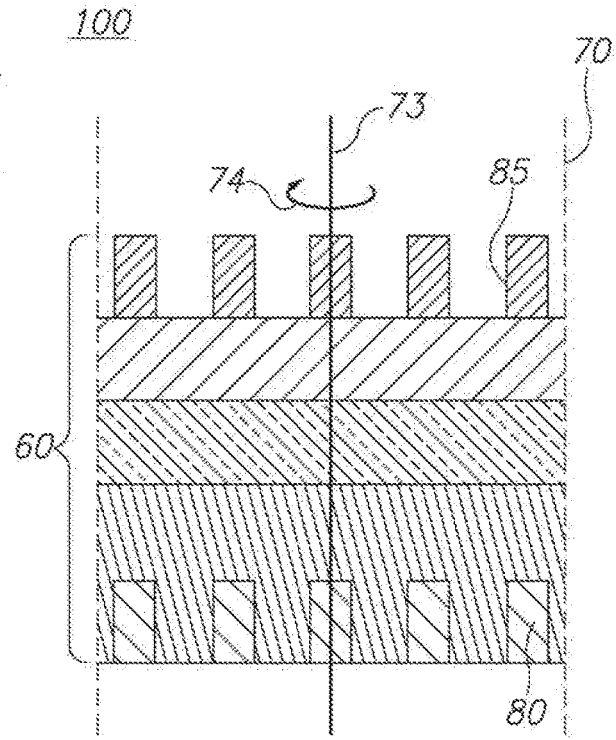
FIG. 2D is a high level schematic cross section illustration of metrology targets having zero offset with periodic structures in two layers, according to some embodiments of the invention.
Figure 2E:
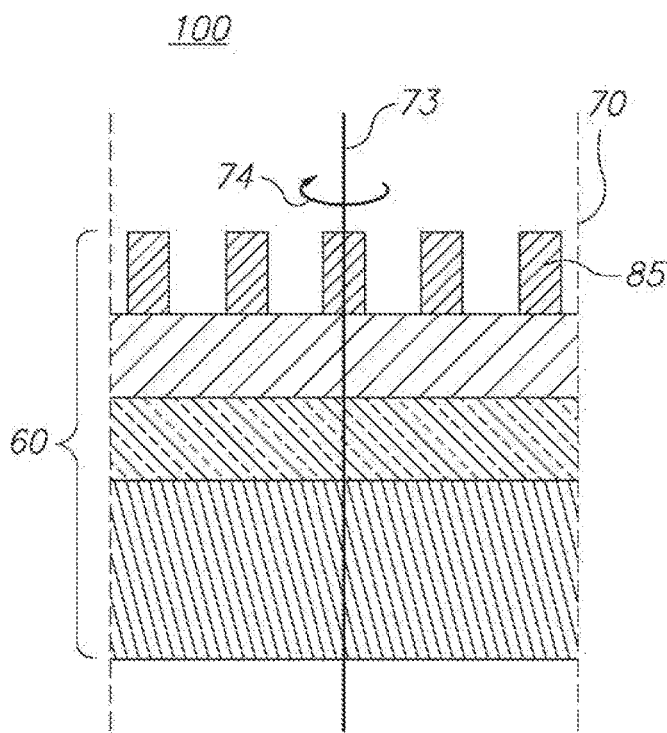
FIG. 2E is a high level schematic cross section illustration of metrology targets having zero offset with periodic structures in one layer, according to some embodiments of the invention.
Figure 2G:
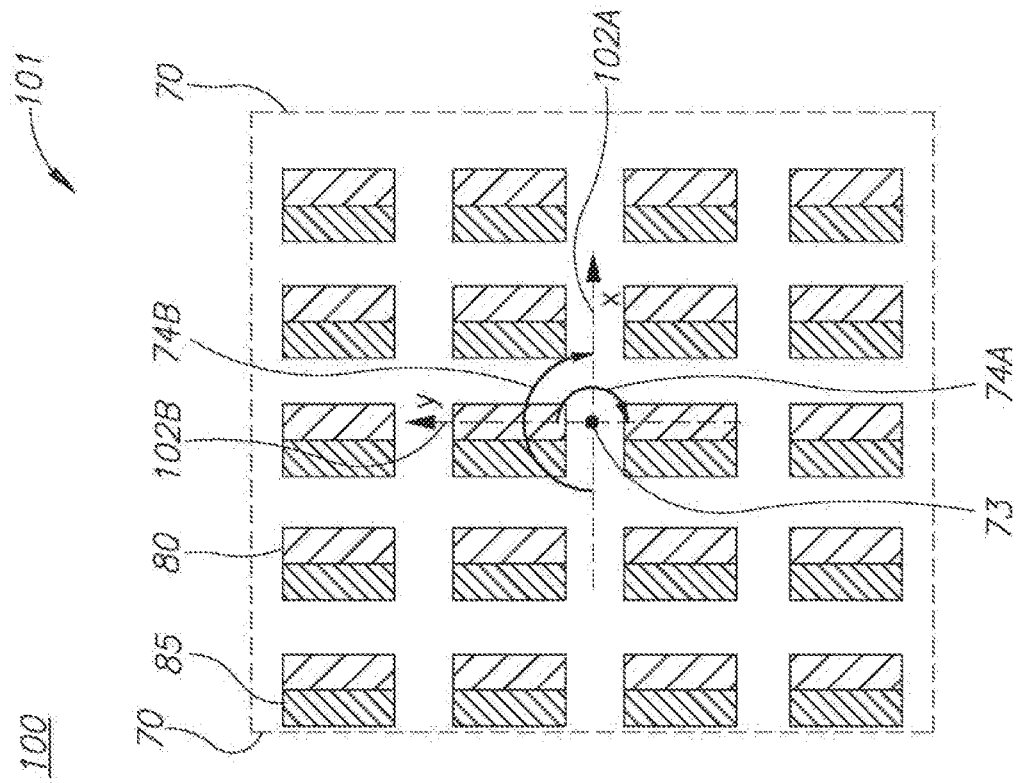
FIG. 2G is a high level schematic illustration of a two dimensional metrology target, according to some embodiments of the invention.
Figure 2F:
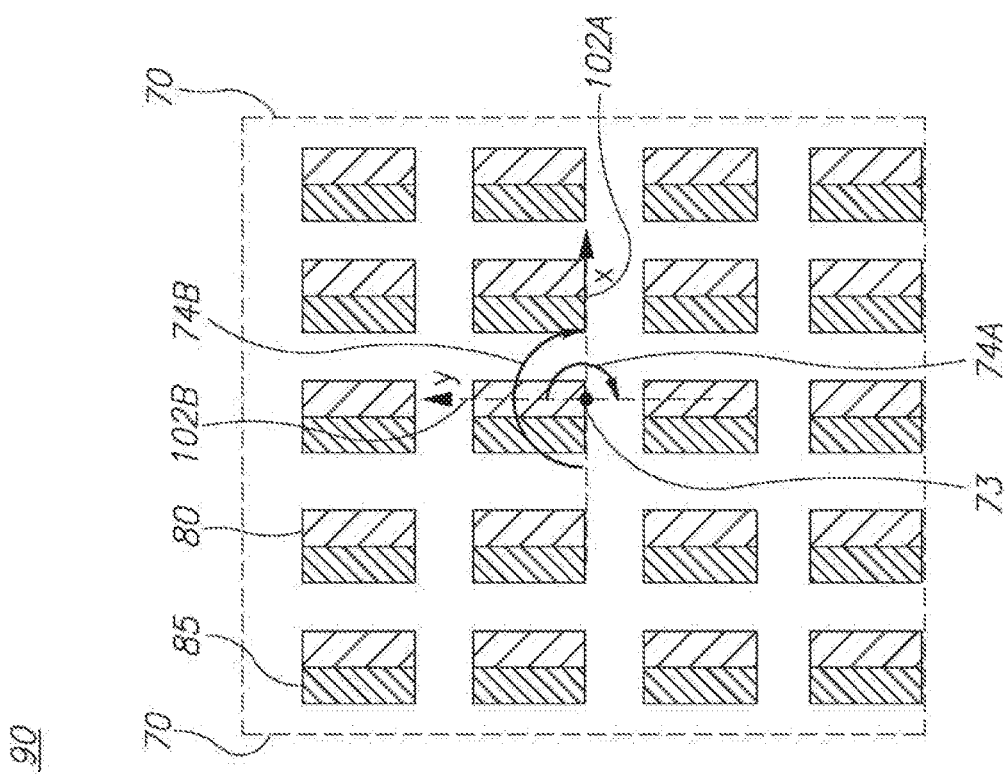
FIG. 2F is a high level schematic illustration of a two dimensional metrology target, according to some embodiments of the invention.

FIGS. 2C-2G and 3A-3D are high level schematic illustrations of metrology targets 100 according to some embodiments of the invention. FIGS. 2B, 2C, 3A and 3C are top views, FIGS. 2D, 2E, 3B and 3D are cross sectional views. FIGS. 2C-2E illustrate target 100 having zero offset and having one cell 101 (FIG. 2D illustrates congruent periodic structures 80, 85 in two layers of cell 100, FIG. 2E illustrates periodic structure 85 in one layer of cell 101 and FIG. 2C is a top view of both), FIGS. 2B and 2G illustrate target 100 having periodic structures in two directions (in two cells and one cell respectively), and FIGS. 3A-B and 3C-D illustrate target 100 having two cells 101A, 101B respectively with opposite designed offsets 107A, 107B respectively. Common to these targets is that at least one of gratings 80, 85 (as non-limiting examples for the periodic structures in the cells) is invariant under a 180° rotation with respect to cell edges 70. Without being bound by theory, this arrangement overcomes the effects of cell edge diffraction, effects which become greater as the cells get smaller, as explained below.

Certain embodiments of the current invention introduce target 100 designs that produce (i) zero signal asymmetries for cells 101 with zero total offset and (ii) in cases where there exists a total offset 107A for cell 101A and a total offset 107B=−offset 107A for cell 101B, the target design leads to signal asymmetry in two cells 107A, 107B that is opposite in sign.

Without being bound by theory, the design of target 100 leads, even in the presence of significant diffractions from cell edges 70, to the following relation:

$$\text{Signal}(180° \text{ rotation(cell with offset)})=\text{Signal(cell with −offset)} \quad \text{(Equation 1);}$$

which also means that:

$$\text{Signal asymmetry(offset)}=-\text{Signal asymmetry(−offset)} \quad \text{(Equation 2); and}$$

$$\text{Signal asymmetry(0 offset)}=0 \quad \text{(Equation 3).}$$

Specifically, instead of target design 90 (FIGS. 1E and 1F), target 100 illustrated in FIGS. 2C and 2D centers edges 70 of cell 101 (as well as its frame, if such is printed), with respect to a 180° rotation 74 about axis 73. In case gratings 80, 85 have a relative offset, one of them, either upper grating 85 or lower grating 80, is invariant to rotation 74 70. Such targets can be printed with or without a frame; one may or may not choose to shift the frame with the programmed offset. In the case of zero offset illustrated in FIGS. 2C and 2D, it is clear that rotating cell 101 by 180° results in a cell with minus the total offset (in this case the total offset is zero, the cell is invariant to 180° rotations, and the signal asymmetry is zero). Thus all three equations above (Equations 1-3) hold.

FIGS. 2C, 2E are high level schematic illustrations of metrology targets 100 in a single layer, according to some embodiments of the invention. FIGS. 2C and 2E are a top view and a cross sectional view, respectively of target 100. (FIG. 2C serves here as a top view of both FIG. 2D and FIG. 2E, as lower grating 80 of FIG. 2D may be understood as being hidden below grating 85 in FIG. 2C.) Targets 100 may comprise single grating 85 or several gratings 85 in a single layer. Cells 101 (e.g. side-by-side cells) may be designed in such a way that their edges 70 (or frame, if that is printed) is centered about rotational symmetry axis 73 of grating 85. Consequently, the rotationally symmetric target design nullifies the inaccuracy that results in the prior art by target edge diffractions (compared to prior art FIGS. 1C and 1D).

In certain embodiments, metrology target 100 comprises at least one cell 101 having at least one periodic structure (e.g., 80, 85 such as a grating) that is invariant with respect to a specified transform with respect to edges 70 of at least one cell 101. In certain embodiments, the specified transform is a 180° rotation 74 about axis 73 perpendicular to at least one cell 101.

In certain embodiments, metrology target 100 comprises at least one cell having at least one grating that is rotationally symmetrical within edges of the at least one cell with respect to a 180° rotation about an axis perpendicular to the at least one cell. In embodiments with more than one grating, the second grating may also rotationally symmetric but it may suffice that it be rotationally symmetric in the absence of the cell edges. In certain embodiments, both cells 101 may be invariant under a 180° rotation about respective axes (e.g., as in FIG. 2C) or about a common axis (e.g., as in FIG. 2A).

In certain embodiments, metrology target 100 may comprise at least one cell 101 having two parallel gratings 80, 85, each at a different layer of target 100, wherein at least one of gratings 80, 85 is rotationally symmetric with respect to axis 73 which is perpendicular to gratings 80, 85 and central with respect to edges 70 of at least one cell 101. Metrology target 100 may comprise one cell 101 with two parallel gratings 80, 85 which are both rotationally symmetric with respect to axis 73 which is central with respect to edges 70 of cell 101.

FIG. 2B is a high level schematic illustration of metrology target 100 having two cells 101A, 101B, each with periodic structures 80, 85 in two dimensions, according to some embodiments of the invention. In certain embodiments, metrology target 100 may comprise at least two cells comprising periodic structures at two directions of the target. For example, metrology target 100 may comprise at least two cells having periodic structures in first of the directions and at least two cells having periodic structures in a second of the directions. For example, metrology target 100 may comprise at least two cells, each having periodic structures in both directions.

FIG. 2G is a high level schematic illustration of a two dimensional metrology target 100, according to some embodiments of the invention. FIG. 2G illustrates a top view of target 100 with cell 101 with an offset between gratings 80, 85, in which one of the gratings (grating 80 in this case) is rotationally symmetric about axis 73 with respect to cell edges 70. As target 100 is two dimensional, at least one grating may be invariant to two 180° rotations 74A, 74B about axis 73 with respect to cell edges 70, and hence at least one grating is centralized with respect to whole cell perimeter 70. In cases with no offset between gratings 80, 85, both gratings may be invariant to 180° rotations 74A, 74B about axis 73, e.g., 180° rotations 74A, 74B may be carried out with respect to a x axis 102A and a y axis 102B of target 100. Targets 100 which are rotationally symmetric may be used as upper or lower gratings in a standard SCOL target, or as a single grating in the case of optical metrology targets that involve single gratings. Similar design symmetry considerations may be applied to other types of two dimensional targets 100.

For the case in which target 100 is a grating-over-grating type of target, SCOL targets 100 may generally comprise N cells 101. For example in technologies that are based on a first order diffraction signal, N is larger or equal to two, while technologies that are based on the zeroth order diffraction signal require that N must be larger or equal to four. All SCOL technologies require that the 180° flip of the cell be equivalent to negating the sign of the offset between the top and bottom grating, and this requirement is broken if the cell is designed such that neither of the gratings, together with its frame is symmetric to 180° rotation. Therefore, to fulfill this requirement, the current invention dictates that in all such SCOL technologies at least one of the gratings is printed in a way that makes it rotationally symmetric to a 180° rotation together with the cell edges.

As illustrated in FIGS. 3A-3D, target 100 may include cells 101A, 101B with programmed offsets 107A, 107B respectively which are opposite in sign. In certain embodiments of the invention, one of the layers may be printed in all cells of same target 100 (for example, the bottom layer) in a way that cell edges 70 (and/or frames, if present) are centered with respect to a 180° rotation 74 of that grating (e.g. bottom grating 80). FIGS. 3A-3D illustrate a simple, non-limiting, example of this case for zero overlay (a case in which the total offset equals the programmed offset) and for two cells 101A, 101B having opposite programmed offset 107A, 107B. Here, rotating cell 101A by 180° results in cell 101B having total offset 107B being minus offset 107A of cell 101A, a fact that makes Equations 1-2 valid even in the presence of diffraction from cell edge 70 (or frame, if present).

Metrology target 100 may comprise two cells 101A, 101B, each comprising a first and a second parallel gratings 80, 85 respectively, in a first and a second layer of target 100, wherein the first gratings (e.g. lower gratings 80) of both cells 101 are rotationally symmetric with respect to axis 73 which is perpendicular to gratings 80, 85 (in each cell 101) and central with respect to edges 70 of the respective cell. The second gratings (e.g. upper gratings 85) may be offset from the respective first gratings at an equal and opposite offset 107.

The pictorial representations above are for the case where edge 70 (and/or frame, if present) of cell 101 is not shifted with upper grating 85. Another option for the target design is to shift edge 70 (and/or frame) with the upper offset, and in that case the new target design still leaves Equations 1-3 valid.

In embodiments, metrology targets 100 may be designed as e.g. scatterometry overlay (SCOL) or optical critical dimension (OCD) targets. SCOL targets 100 may comprise four cell or eight cell targets or any number N of cells where N depends on the technology. Targets 100 may comprise cells 101 in a single layer, in two layers or in more than two layers. Targets 100 may have their top views comprised of one dimensional gratings or of two dimensional gratings. In particular, targets 100 may comprise at least four cells 101 arranged in two dimensions of target 100. Targets 100 may comprise no offset between cell elements (e.g. gratings 80, 85), a single offset between cell elements, or multiple offsets. Targets 100 may comprise at least n gratings 80, 85 and be designed to have at least k offsets among the gratings (with k<n).

Advantageously, the inventors have found out that targets 100 having their design following the disclosed rules produce more accurate results for the overlay measurement. The causes for inaccuracy, which are left to be corrected, merely comprise e.g. de-centering of the illumination around the cell center, light contamination from the surrounding of the cell (which is not expected to be symmetric to 180° rotation), and grating asymmetries (such as differences in the left and right side wall angles of each bar).

FIG. 4 is a high level flowchart illustrating a metrology target design method 200, according to some embodiments of the invention. Method 200 comprises designing and/or producing at least one metrology target cell comprising at least one cell having at least one periodic structure that is invariant with respect to a specified transform (e.g., a 180° rotation about an axis perpendicular to the at least one cell) with respect to edges of the at least one cell.

In embodiments, method 200 comprises producing at least one metrology target cell having at least one grating that is symmetrically positioned within edges of the at least one cell with respect to both a reflection and a 180° rotation around an axis perpendicular to the at least one cell.

In embodiments, method 200 may comprise designing and/or producing a rotationally symmetric metrology target cell with reference to the cell edges (stage 210); designing and/or producing a metrology target cell to be rotationally symmetric with respect to one grating and have another grating offset therefrom (stage 212); designing and/or producing a metrology target cell having some of its features rotationally symmetric with respect to the cell edges (stage 214); designing and/or producing metrology targets having multiple cells with elements that are invariant under a specific transform with respect to the corresponding cell boundaries (stage 215) and designing and/or producing metrology target cells which are symmetric to a 180° rotation with respect to at least some of their features (e.g. one grating) (stage 218), and as a non-limiting example for such a transform.

Method 200 uses rotationally symmetric or partially rotationally symmetric target cells for overlay measurements (stage 220), to reduce an error in overlay measurements (stage 225).

Embodiments of the invention comprise metrology systems arranged to measure at least one metrology target 100 as described above, and metrology target design and production system operating according to method 200, as well as software tools used to design and produce targets 100 or implement method 200.

Side by Side Paradigm

FIG. 5A is a highly schematic illustration of the side by side paradigm explained below, according to some embodiments of the invention. FIG. 5A schematically illustrates a source 40 and a beam splitter 42 arranged to generate at least two illumination beams 169A, 169B that illuminate respective target cells 101A, 101B and yield respective reflected spots or collection beams 170A, 170B which interfere at the pupil plane of a detector 59 to yield at least one non-zero diffraction order. Illustrated are the zeroth and ±1$^{st}$ diffraction orders as a non-limiting example. In the path of at least one of beams 169A, 169B, 170A, 170B, a modulator 43 may be set to enable extraction of the overlay error between cells 101A, 101B. Various embodiments of modulator 43 are presented in the examples below, FIG. 5A schematically illustrates, in a non-limiting manner, one of the examples, namely a phase modulator in the path of illumination beam 169B. Generally n≥1 orders of diffraction may be measured and analyzed. Further indicated in FIG. 5A are some of the parameters which are explained below.

Without being bound by theory, the following derivation provides a basis for various measurement techniques which are described below. In the side-by-side SCOL paradigm the overlay information is contained in the interference terms between the electromagnetic fields reflected off the two side-by-side cells in the collection pupil. Specifically, the electric field of the n$^{th}$ diffraction order reflected by layer 'a', in the collection pupil, is denoted by $$|E_n^{(a)}(\vec{k})|e^{i\psi_n^{(a)}(\vec{k})}.$$

Here $|E_n^{(a)}(\vec{k})|$ is the amplitude of the field and $\psi_n^{(a)}(\vec{k})$ is its phase, both with respect to the position in the pupil plane denoted by k. The total intensity present at the collection pupil point $\vec{k}$ and diffraction order n, is then given by the following expression (here and below the collection pupil coordinates are denoted in terms of illumination pupil coordinates, and so, for example, the intensity at the center of the +1st order is denoted by $I_{n=+1}(\vec{k}=0)$).

$$I_n(\vec{k}) = |E_n^{(1)}(\vec{k})|^2 + |E_n^{(2)}(\vec{k})|^2 + \qquad \text{(Equation 4)}$$
$$2|E_n^{(1)}(\vec{k})||E_n^{(2)}(\vec{k})|\cos\left(\frac{2\pi \cdot (OVL + \text{Offset}) \cdot n}{\text{Pitch}} + \psi_n^{(1)}(\vec{k}) - \psi_n^{(2)}(\vec{k}) + \vec{k} \cdot \vec{X} + \varphi_1 - \varphi_2\right),$$

where OVL is the relative overlay between gratings 85, Offset is the programmed offset between gratings 85 in direction 102 of the overlay, $\vec{X}$ is the relative distance between the centers of the symmetric parts of the spots (which is taken to be equal to the distance between the centers of the cells, see FIG. 2A), and $\varphi_a$ is the phase in illumination of the beam falling on grating (a).

Clearly, the overlay information is present in the argument of the cosine, or more precisely, in the difference of the argument of the cosine at diffraction order +1 and −1. In particular, the side-by-side technology uses the fact that for targets whose symmetry is non-damaged (rotationally symmetric gratings) the phases obey the following symmetry relation:

$$\psi_n^{(a)}(\vec{k}) = \psi_{-n}^{(a)}(-\vec{k}). \qquad \text{(Equation 5)}$$

Relying on this fact, a multitude of techniques is described below, for extracting the overlay from the intensity in the pupil. It is noted in passing that for targets having non-damaged symmetry (rotationally symmetric gratings), the amplitude of fields also obeys symmetry of the following form.

$$|E_n^{(a)}(\vec{k})| = |E_{-n}^{(a)}(-\vec{k})|. \qquad \text{(Equation 6)}$$

FIG. 13 is a high level schematic flowchart illustrating a metrology method 500, according to some embodiments of the invention. Method 500 may comprise estimating an overlay error between at least two layers by carrying out at least one of the following stages: illuminating a side by side metrology target (stage 450) that comprises at least two periodic structures which are at different layers, are along a common measurement direction and have a same pitch. The target may be made invariant under a transformation such as at least one 180° rotation (stage 457), i.e., invariant to a 180° rotation about an axis that is perpendicular to the target. For example, the metrology target may be configured to satisfy Equation 5. Method 500 may further comprise carrying out the illumination simultaneously with respect to the periodic structures (stage 465), measuring interference of at least one diffraction order from the at least two periodic structures (stage 470); and extracting the overlay error from the measured interference (stage 480).

In certain embodiments, method 500 may further comprise introducing a controlled variable that effects the illumination and/or collection beams from at least one of the periodic structures (stage 460) and extracting the overlay error from the measured interference with respect to the introduced controlled variable (stage 485). Finally, method 500 may comprise estimating an overlay error between at least two layers with the periodic structures (stage 490).

Introducing a controlled variable is to be understood in a broad sense. In certain embodiments, the controlled variable may be a phase φ introduced by phase modulator 43 (see e.g., Example 5 below). In certain embodiments, the controlled variable may be an image shift in any plane (see e.g., Example 2 below for image shifts in the field plane). In certain embodiments, the controlled variable may be additional measurements and/or additional targets that allow extracting the overlay from multiple measurement results (see e.g., Example 1 below).

The controlled variable, such as phase φ, may be used to calibrate metrology system 110 on the fly with respect to the measured targets. In certain embodiments, the distance X between the periodic structures may also be designed to calibrate metrology system 110.

In certain embodiments, side by side targets 100 may be different parts of a single periodic structure, e.g., two regions of a single grating 85.

FIG. 5B is a high level schematic illustration of a metrology system 110 that may be adapted to measure targets 100, according to some embodiments of the invention. FIG. 5B serves as a basis for various implementation possibilities which are described below. Any other form of a metrology system could be adjusted with the side by side components for the equivalent system. Metrology system 110 may comprise an illumination arm 45 arranged to illuminate metrology target 100 that comprises at least two periodic structures 85 which are at different layers, are along a common measurement direction 102 and have a same pitch 103 (with metrology target 100 being symmetric with respect to a 180° rotation 74 about axis 73 that is perpendicular to target 100). Illumination arm 45 is arranged to carry out the illumination simultaneously with respect to periodic structures 85, e.g., by splitting a spot from a light source 40. Metrology system 110 may further comprise a collection arm 55 arranged to measure interference of at least one diffraction order from the at least two periodic structures; and a processor 111 arranged to extract an overlay error from the measured interference.

In metrology system 110, a light beam from a light source 40 enters a spot splitting apparatus 42 which has all required optics and apertures to generate at its exit a number of beams with designed spatial and angular content (e.g. beam diameter, shape, phase, divergence and polarization). As noted above, multiple beams may be generated either from multiple coherent sources or via spot splitting apparatus 42. Illumination arm 45 includes all components or systems (optical, mechanical, electrical or other) required to enable the operation of system 110 according to any implementation as exemplified below for non-limiting possible variations. The light then goes through a beam splitter 54 into an objective 51 (e.g. a high NA objective). Then, the light is reflected (diffracted) off side by side SCOL target 100, through objective 51, beam splitter 54 and collection arm 55, which includes all required components and systems required for signal detection according to the relevant operational option. After passing collection arm 55 the light falls onto a detector 59 (e.g. a camera). Detector 59 may be either in a pupil conjugate plane or in a field conjugate plane. In certain embodiments, illumination arm 45 and/or collection arm 55 may comprise a scanning mechanism in wither the field or pupil planes.

Spot Splitting

There are a few ways of splitting the illumination spot from source 40, which are illustrated in the following for splitting the illumination beam into two beams as a non-limiting example (clearly splitting to more beams is straightforward). All subsystems also include the required optics and apertures to generate spots on target 100 that have the required illumination NA (numerical aperture), size and distribution and polarization.

Figure 6A:
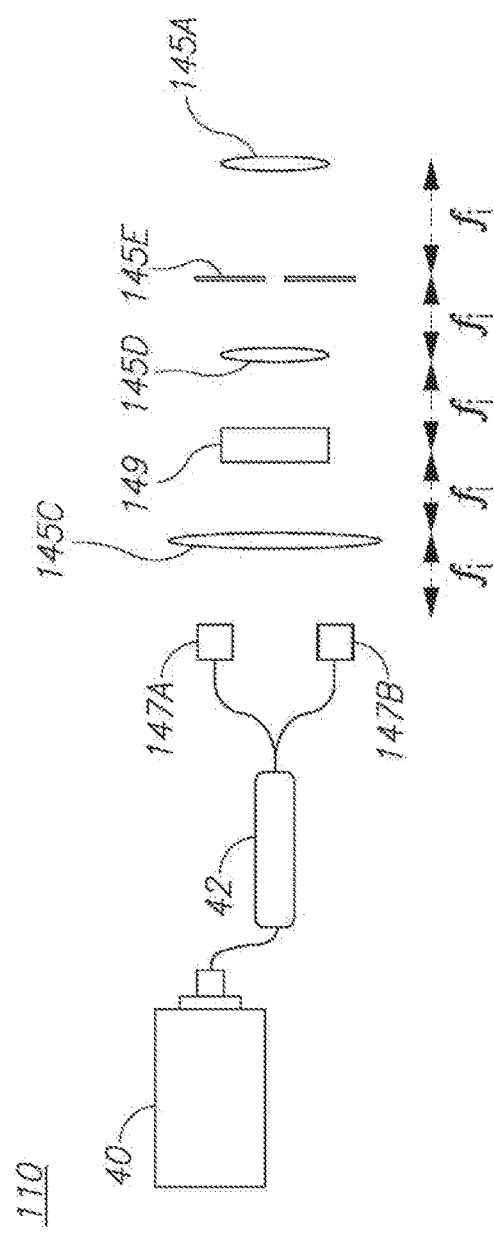
FIG. 6A is a high level schematic illustration of a beam splitter with a phase modulation unit in the illumination arm of a metrology system, according to some embodiments of the invention.

FIG. 6A is a high level schematic illustration of a beam splitter 42 with a phase modulation unit 147 in illumination arm 45 of metrology system 110, according to some embodiments of the invention. In the illustrated example, beam splitter 42 comprises a fiber beam splitter and each of the illumination beams (collimated or not) may be directed through respective phase modulation sub-unit 147A, 147B. Phase modulation sub-unit 147A, 147B may be arranged to manipulate both amplitude and phase or only the phase of the amplitude is regulated. The main advantages of such embodiments are that they are not sensitive to vibrations and enable performing various manipulations (e.g. phase shifts) before exiting the fiber, which increase robustness. The fibers can be either: single mode, multimode, polarization maintaining, photonic crystal, waveguides or any other type of light guides (solid or liquid). The distance between the spots could be controlled by adjusting the distance between the fiber outputs. Further illustrated parts of illumination arm 45 comprise lens 145C, apodizer 149, lens 145D, illumination field stop 145E and exit lens 145A.

Figure 6B:
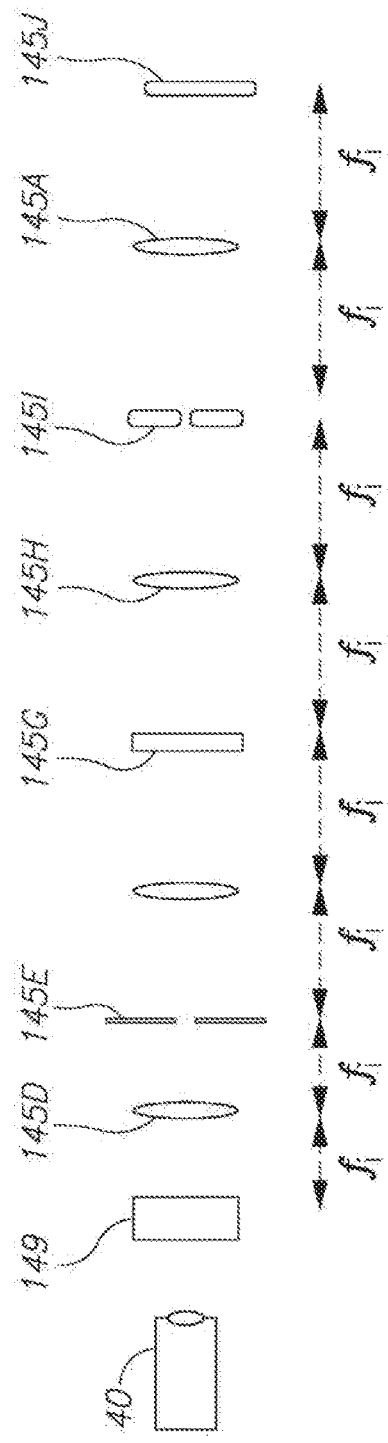
FIG. 6B is a high level schematic illustration of a beam splitter in the illumination arm of a metrology system, according to some embodiments of the invention.

FIG. 6B is a high level schematic illustration of a beam splitter 42 in illumination arm 45 of metrology system 110, according to some embodiments of the invention. In the illustrated example, beam splitter 42 is implemented as a grating spot splitter. The beam from light source 40 (e.g. a collimated laser beam) passes through a grating 145G and is split into orders of the grating from which two may be optically chosen (e.g. ±1st orders, 0 and 1st orders) to provide the two illumination beams serving as the spots. FIG. 6B further illustrates the following elements of illumination arm 45: apodizer 149, lens 145D, illumination field stop 145E and lens before grating 145G and lens 145H, filters 145I, lens 145A and filters 145J used to select the refracted beams and prepare them as illumination beams. Grating 145G may be an amplitude grating or a phase grating; a flat or a volume grating; a fixed grating (yielding a fixed distance between spots), a set of fixed gratings (allowing different distances), or an adjustable grating (allowing for a continuous change of differences as well as a change in inter-spot intensity). Possible grating 145G types comprise acousto-optic gratings, electro-optic gratings, piezo-electric gratings, pyro-electric gratings, or SLM (Spatial Light Modulation) generating grating patterns (e.g. MEMS, liquid crystals etc.).

FIG. 6C is a high level schematic illustration of a beam splitter 42 in illumination arm 45 of metrology system 110, according to some embodiments of the invention. In the embodiment illustrated in FIG. 6C, two prisms 42A, 42B may be used as a double Wollaston prism which allows for distance variation via the distance change between the two prisms as well as the control of inter-spot intensity difference via a polarizer and a half wave plate which dictate the state of polarization incident upon first Wollaston prism 42A. Another advantage of this design is the fact that the two beams have orthogonal polarization. Other prism based options comprise e.g., Soleil-Babinet compensator, Nomarski prism, beam displacement prisms, Glan-Thompson.

FIG. 6D is a high level schematic illustration of a beam splitter 42 in illumination arm 45 of metrology system 110, according to some embodiments of the invention. In the embodiment illustrated in FIG. 6D, a simple beam splitter is presented, having beam splitting element 42C and mirror 42D. The construction could be either in free space with the possibility of changing the inter-beam distance by simply moving or tilting mirror 42D, or a monolithic construction for preventing any vibration differences between the two beams. Any other beam splitting prism may also be used in this context.

In certain embodiments, beam splitter 42 may be arranged to yield multiple illumination beams 169 and/or to allow splitting the illumination beam (i.e. electromagnetic radiation from at least one source 40) into two (or more) out of a range of N possible illumination beams. Beam splitter 42 and/or illumination arm 45 may be arranged to controllably yield and direct illumination beams 169 at selected periodic structures 85. For example (see FIG. 12B, 12C below) beam splitter 42 may be arranged to illumination beams 169A, 169B to illuminate any of multiple cells 101 on different layers of the wafer. In certain embodiments, targets 100 may have an arbitrary relative position vector $\vec{r}$ and beam splitter 42 may be arranged to controllably generate illuminating beams to specified values of the position vector. Beam splitter 42 may be implemented by a single or composite beam splitting mechanism and may be arranged to control the position and size of each of the illumination spots.

EXAMPLES—TECHNIQUES AND APPARATUS CONFIGURATIONS

The following are non-limiting examples for metrology method stages, techniques and apparatus configurations for measuring side by side targets 100 according to the side by side paradigm, referring to Equation 4 presented above. These examples illustrate different ways to extract the overlay OVL from the intensity measurements, and more particularly from the argument of the cosine in Equation 4, namely:

$$\frac{2\pi \cdot (OVL + \text{Offset}) \cdot n}{\text{Pitch}} + \psi_n^{(1)}(\vec{k}) - \psi_n^{(2)}(\vec{k}) + \vec{k} \cdot \vec{X} + \varphi_1 - \varphi_2.$$

Illumination arm 45, collection arm 55 and processor 111 may be arranged to implement the principles presented below, as well as any combination or variation of these principles.

Example 1—Multiple Measurements

In certain embodiments, method 500 comprises setting the illumination beams to exhibit no phase differences (stage 510) i.e. setting $\varphi_{1,2}=0$; illuminating separately each periodic structure to measure the respective diffracted intensity (stage 512), i.e. illuminating grating (1) alone to provide a measurement of $|E_n^{(1)}(\vec{k})|$ and illuminating grating (2) alone to provide a measurement of $|E_n^{(2)}(\vec{k})|$ (e.g. by turning off the beams illuminating the other grating respectively); illuminating simultaneously the periodic structures to measure the interference term (stage 514) of Equation 4 and extracting the overlay from interference measurements for ±1 diffraction orders and opposite locations ±k (stage 516).

For example, stage 516 may be carried out as follows: Extracting the cosine $$C_n(\vec{k}) = \cos\left(\frac{2\pi \cdot (OVL + \text{Offset}) \cdot n}{\text{Pitch}} + \psi_n^{(1)}(\vec{k}) - \psi_n^{(2)}(\vec{k}) + \vec{k} \cdot \vec{X}\right)$$

for each order n=+1, n=−1. From the cosines, extracting the two mathematically consistent arguments of the cosine, $\beta_n(\vec{k})=\pm a\cos(C_n(\vec{k}))$. From the two mathematically consistent candidates for $\beta_{+1}(\vec{k})$ and the two candidates for $\beta_{-1}(-\vec{k})$, producing four candidates for $$\Delta\beta(\vec{k}) = \frac{4\pi \cdot (OVL + \text{Offset})}{\text{Pitch}} + 2\vec{k} \cdot \vec{X}.$$

In certain embodiments, these measurements may be carried out with polarized or un-polarized light. If polarized, the polarization of beams (1) and (2) can be identical or different, and if the two polarizations are orthogonal, a polarizer may be used at collection arm 55. The polarization of the beams may be linear or polar (radial/azimuthal).

Extracting the overlay may be carried out by symmetrizing all the candidate functions $$\Delta\beta(\vec{k}) \rightarrow \frac{1}{2}[\Delta\beta(\vec{k}) + \Delta\beta(-\vec{k})]$$

and using the statistical distribution of $\Delta\beta(\vec{k})$ across the pupil coordinate $\vec{k}$ to find the correct solution which gives the constant function $$\Delta\beta(\vec{k}) = \frac{4\pi \cdot (OVL + \text{Offset})}{\text{Pitch}}.$$

This choice may be simplified by choosing a programmed offset judicially to simplify the extraction (stage 518). Finally, the collection pupil may be calibrated to remove from each of the four candidates for $\Delta\beta(\vec{k})$ the function $2\vec{k} \cdot \vec{X}$.

Extracting the overlay may be carried out by using three periodic structures, one in one layer and two in another layer with different programmed offsets (stage 520) and extracting the overlay from interference measurements for ±1 diffraction orders and the two structures in the same layer with different programmed offsets (stage 522). Denoting the target in layer no. 1 as cell I and the two cells in layer no. 2 as cell II and cell III, each of cells II and III has a different programmed offset with respect to cell I. Performing the measurements of stages 512 and 514 for both cell pairs (I-III) and (II-III), two cosines are obtained for the two relative offsets OF(I-III) and OF(II-III) in both the plus and minus first orders. These four cosines have only one solution for the overlay that is mathematically consistent.

Extracting the overlay may be carried out by taking multiple measurements with different illumination intensities (stage 524) and extracting the overlay from interference measurements for ±1 diffraction orders and the different illumination intensities (stage 526). The multiple measurements with different relative intensities between the two spots provides sufficient information to extract the cosines $C_n(\vec{k})$.

FIG. 7 is a high level schematic illustration of a metrology system 110 that may be adapted to measure targets 100 in the multiple measurements example, according to some embodiments of the invention. In the illustrated examples, polarizers 145B, 155A may be inserted in association with illumination arm 45 (e.g. in front of an exit lens 145A thereof) and in association with collection arm 55 (e.g. before an entrance lens 155B, collection field stop 155C or before or after exit lens 155D) respectively.

Example 2—Compensated Field Shifts

In certain embodiments, method 500 comprises setting the illumination beams to exhibit no phase differences (stage

510) i.e. setting $\varphi_{1,2}=0$; imaging the wafer to a field conjugate plane (stage 530) and performing image shifting at the field conjugate plane (stage 532), e.g. by modifying the image to shift the image part containing one of the gratings in the direction of the grating by N different shifts, with N≥3, compensating for the image shifting in the illumination (stage 534) and extracting the overlay algorithmically from the compensated image shifts (stage 536).

The following non-limiting example illustrates the method with N=4 and $$Offset_a = \frac{Pitch}{4} a,$$

with a=0,1,2, and 3. As the generalization to N=3 and N≥5 is straightforward the following calculated can be easily adjusted.

Image shifting 532 may be compensated by shifting the illuminating beam in an opposite direction, to maintain the overall position of the image unchanged (stage 534). For example, the laser beam falling on the cell, whose image is shifted, may be shifted back in illumination branch 45, so that its position in the field conjugate plane after the image shifting stage is unchanged.

The algorithmic extracting of the overlay may be carried out using the N different collection pupil images in any of the following non-limiting ways. Other algorithms and algorithm combinations may be optimized with respect to performance requirements of the system.

Algorithm (I): For each diffraction order n=±1, and each illumination pixel $\vec{k}$, use linear combinations of the N signals to extract two differential signals, $D_{1,2}$ which are proportional to the cosine and the sine of the phase $$\beta_n(\vec{k}) = \frac{2\pi \cdot OVL \cdot n}{Pitch} + \psi_n^{(1)}(\vec{k}) - \psi_n^{(2)}(\vec{k}) + \vec{k} \cdot \vec{X},$$

respectively. The amplitude of these differential signals is proportional to the amplitude of the fields, $|E_n^{(1,2)}(\vec{k})|$, but is independent of the phases $\psi_n^{(1,2)}(\vec{k})$. Next, for each order, construct the per-pixel complex number $D_1+_iD_2$, whose phase is equal to $\beta_n(\vec{k})$. Finally, using the difference $\Delta\beta(\vec{k})=\beta_{+1}(\vec{k})-\beta_{-1}(-\vec{k})$, and assuming the symmetry properties of the phases $\psi_n^{(1,2)}(\vec{k})$, extract the overlay by either writing $$OVL = \frac{p}{8\pi}[\Delta\beta(\vec{k}) + \Delta\beta(-\vec{k})],$$

or by calibrating the pupil, and subtracting 2 $\vec{k}\cdot\vec{X}$ from each $\beta_n(\vec{k})$.

Algorithm (II): For each illumination pixel $\vec{k}$, use the 2N signals obtained from the $+1^{st}$ and $-1^{st}$ orders of the N field offsets, to form four linear combinations; two that are proportional to the sine of $$\gamma(\vec{k}) \equiv \frac{2\pi \cdot OVL}{Pitch} + \vec{k} \cdot \vec{X},$$

and two that are proportional to the cosine of $\gamma(\vec{k})$. For example, if N=4, these four combinations are proportional to the amplitudes $|E_n^{(1,2)}(\vec{k})|$; also two of the combinations (denoted as $\sigma_{1,2}(\vec{k})$) are proportional to the cosine of $\Delta\psi=\psi_{+1}^{(1)}(\vec{k})-\psi_{+1}^{(2)}(\vec{k})$ and the other two (denoted as $\delta_{1,2}(\vec{k})$) to the sine of $\Delta\psi$. From these four differential signals produce two complex numbers, whose phase is $\gamma(\vec{k})$ and obtain two independent determinations of the OVL (both can be obtained by either symmetrizing $\gamma(\vec{k})\to\gamma(\vec{k})+\gamma(-\vec{k})$ or by performing a pupil calibration and subtracting from $\gamma(\vec{k})$ the function $\vec{k}\cdot\vec{X}$). Use these two overlay determinations to form a weighted average overlay determination.

Algorithm (III): Form two combinations from the squares of $\sigma_{1,2}(\vec{k})$ and $\delta_{1,2}(\vec{k})$ defined above such that their size is independent of $\Delta\psi$. These two combinations are proportional to the cosine of $\gamma(\vec{k})$ and to its sine, respectively, and this allows one to extract the phase $\gamma(\vec{k})$ itself. To determine the overlay proceed as described in Algorithm (II).

Algorithm (IV): For each diffraction order and each pupil coordinate, form two linear combinations with pre-determined coefficients that are optimized to reduce system noise and that follow any of the well-known phase shifting algorithms in the analysis of interferometric signals. These two combinations are proportional to the sine and the cosine of $\beta_n(\vec{k})$ from Algorithm (I). Use these linear combinations in the same way as Algorithm (I) uses them.

FIG. 8A is a high level schematic illustration of a metrology system 110 that may be adapted to measure targets 100 in the compensated field shifts example, according to some embodiments of the invention. In the illustrated example, illumination arm 45 and collection arm 55 may comprise respective field shift modules 146, 156 which may be coordinated by a feedback and control unit 160. Field shift modules 146, 156 may comprise, beside the field shift mechanism, all relevant components and systems (e.g. optics and mechanics) to enable correct illumination on target 100 on substrate 50 and correct imaging of the required signal on the detector.

In certain embodiments, compensated field shifts may be combined with multiple measurements (see Example 1 above), for example in the following ways. One or more of the measurements in the multiple measurements example may be taken with a nonzero compensated field shift (stage 528) to remove ambiguities in the overlay measurements and improve sensitivity, or one or more additional measurements may be taken with a nonzero phase shift (stage 529) to remove ambiguities and improve sensitivity.

In certain embodiments, these measurements may be carried out with polarized or un-polarized light. If polarized, the polarization of beams (1) and (2) can be identical or different, and if the two polarizations are orthogonal, a polarizer may be used at collection arm 55. The polarization of the beams may be linear or polar (radial/azimuthal).

Figure 8C:
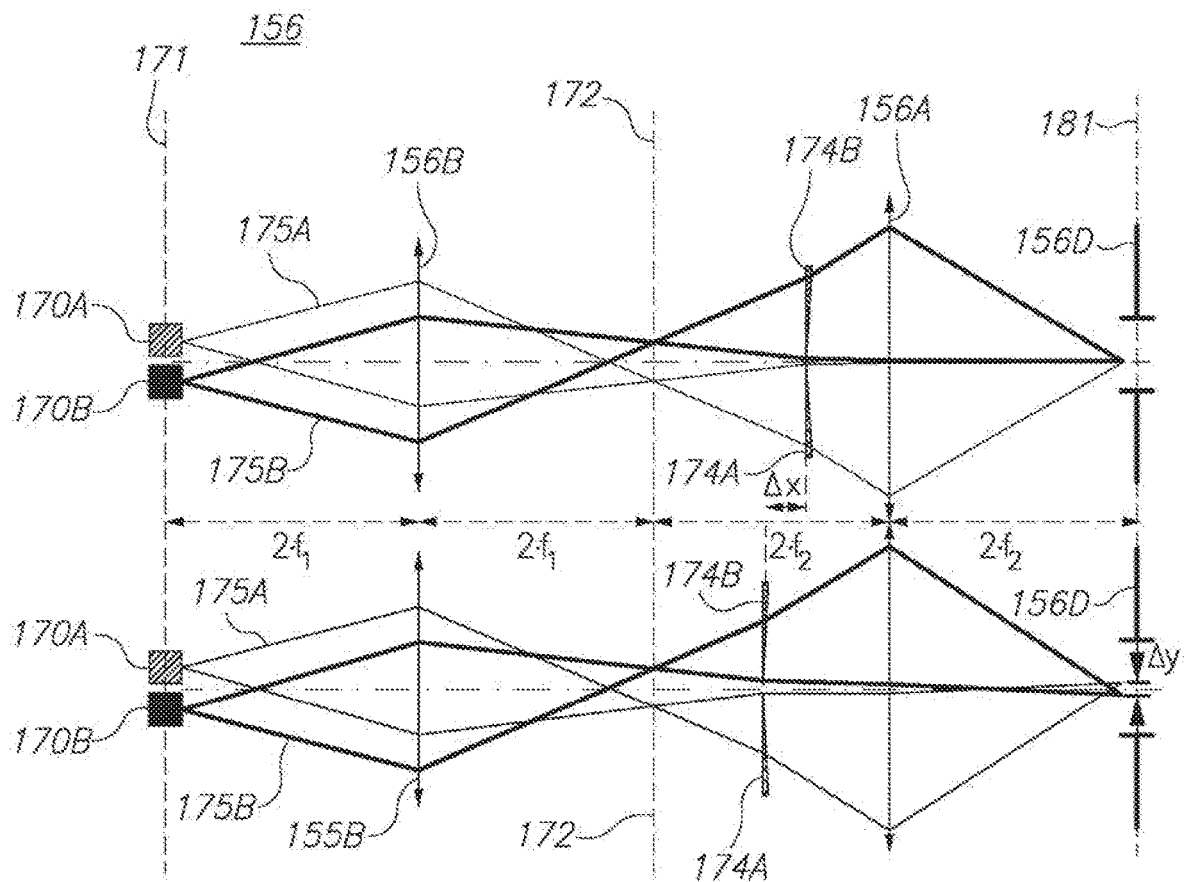
FIG. 8C is a high level schematic beams tracing illustration of field shifting mechanisms in the collection arm, according to some embodiments of the invention.

FIG. 8B is a high level schematic illustration of field shifting mechanism 156 in collection arm 55 according to some embodiments of the invention. Field shifting mechanism 156 is applicable e.g., in Examples 2-4. FIG. 8B illustrates schematically a possible configuration of collection arm 55 comprising, between field stop 155C at plane 171 and field stop at plane 181, a set of lenses 156A, 156B etc. with intermediate optical elements 194 (e.g. prisms 174 or 184) as explained below with respect to non-limiting examples presented in FIGS. 8C and 8D. Distances between lenses 156A, 156B etc. may be configured as focal lengths (e.g., $f_1$, $f_2$, $f_3$ in FIG. 8B) or as double focal lengths (e.g., $f_1$, $f_2$, and $f_{1A}$, $f_{1B}$, $f_2$ in FIGS. 8C, 8D, respectively) depending whether the optics are used to generate Fourier transforms or images respectively, and do not limit the scope of optical implementation. It is noted that the indices of the focal length are not necessarily consistent between different figures and merely represent examples for certain optical arrangements.

Figure 8D:
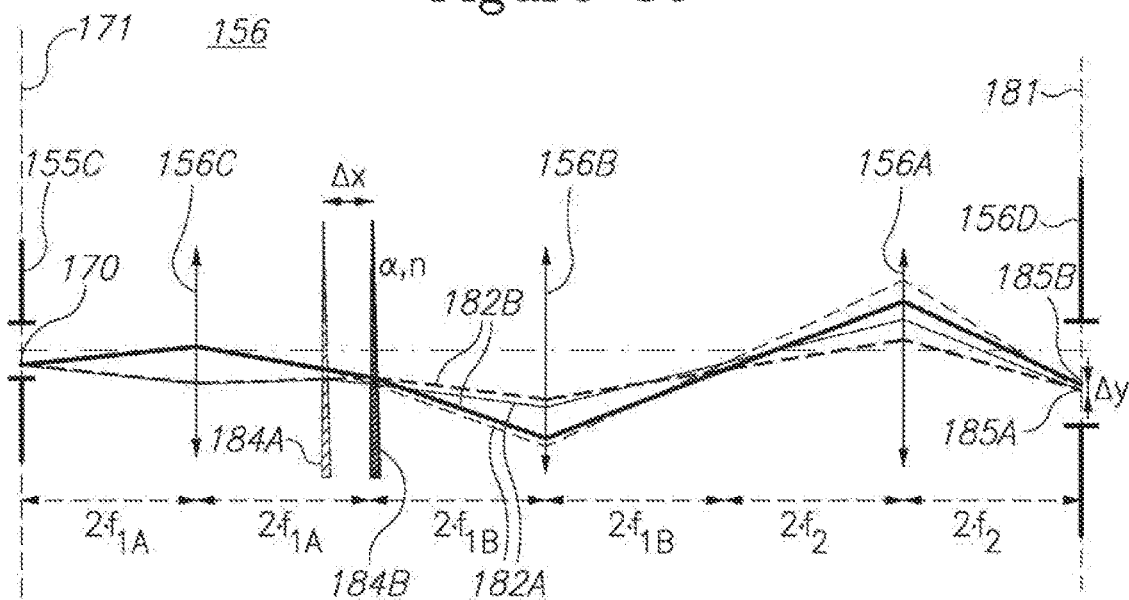
FIG. 8D is a high level schematic beams tracing illustration of field shifting mechanisms in the collection arm, according to some embodiments of the invention.

FIGS. 8C and 8D are high level schematic beams tracing illustrations of non-limiting examples for field shifting mechanisms 156 in collection arm 55 according to some embodiments of the invention. These examples may also be used, with necessary modifications, for field shifting mechanism 146 in illumination arm 45. The two examples presented in FIGS. 8C and 8D may be replaced by other optical arrangements.

FIG. 8C illustrates a configuration with prisms 174A, 174B as optical element 194 used to offset beams 175A, 175B with respect to each other (each corresponding to a periodic structure 85 or cell 101 in target 100, denoted at plane 171 as spots 170A, 170B), according to some embodiments of the invention. The top and bottom parts of FIG. 8C illustrate alternative positions of the prisms. When prisms 174A, 174B are placed after plane 172, they cause an offset of the image at plane 181. Split prisms 174A, 174B are placed to diffract only the respective beam 175A, 175B. Thus, each wedge prism 174A, 174B effects only the respective image 170A, 170B of one of cells 101 and hence yields an offset between the two images ($\Delta y$ at plane 181). The position of prisms 174A, 174B determines the extent of the offset, as illustrated in the two beam tracing diagrams in FIG. 8C.

FIG. 8D illustrates a configuration with prism 184 at two positions 184A, 184B as optical element 194 used to offset beams 182A, 182B imaging a periodic structure 85 or cell 101 in target 100, denoted at plane 171 as spots 170A or 170B, according to some embodiments of the invention. FIG. 8D illustrates both alternative positions of prism 184 as prisms at positions 184A, 184B. Prism 184 is characterized by its wedge angle $\alpha$ and refractive index n and its relative position $\Delta x$ determines the offset $\Delta y$ of the image at plane 181, as illustrated by the beam tracings 182A, 182B corresponding to different positions 184A, 184B, respectively. This embodiment is implemented using three intermediate lenses 156A, 156B, 156C and can clearly be used in either collection arm 55 or illumination arm 45 in any of the field offset examples. In certain embodiments, FIG. 8D illustrates shifting one of spots 170A, 170B, and an additional prism with an angle opposite to prism 184 (similarly to the difference in orientation between prisms 174A, 174B) or a different refractive index n may be positioned on the optical path to shift another one of spots 170A, 170B, e.g. in an opposite direction, implementing a split prism configuration.

FIG. 8E is a high level schematic illustration of metrology system 110 with compensated field shifting according to some embodiments of the invention. In the compensated field shifting example, the illumination beam on target cell image is shifted to compensate for the field shifting, as explained above. FIG. 8E hence illustrates illumination arm 45 with a beam shifting module 146 with respective lenses and optical elements 194 which may be configured along the same principles that were explained in relation to the collection arm field shifting (FIGS. 8C, 8D).

FIG. 8F is a high level schematic illustration of a two dimensional arrangement of optical elements 194, according to some embodiments of the invention. Optical elements 194 may be configured to shift images of a two dimensional cell array (as illustrated e.g. in FIGS. 2B, 12A-12C) for example wedge or split prisms 174 or 184 may be oriented according to the arrows in FIG. 8F. For example, split prisms 184 may be built to facilitate both x and y targets at the same time as well as all cells at the same time for a four cell target.

Example 3—Wafer Shifts

In certain embodiments, method 500 comprises performing image shifts physically (stage 538) and extracting the overlay algorithmically along principles similar to the ones described in Example 2. Generally, physical image shift, carried out by moving the wafer, may replace all or some of the N signals described above. In certain embodiments, images of each side-by-side cell couple may be taken once, without any spot compensation procedure.

Example 4—Uncompensated Field Shifts

In certain embodiments, method 500 comprises processing uncompensated shifted images with respect to phases which are dependent on the pupil coordinates (stage 540) and calibrating the pupil to calculate the phase and extract the overlay therefrom (stage 542). Instead of shifting the image in the conjugate field plane by N≥3 amounts $\Delta_{a=1,2, \ldots, N}$ and shifting the spot back on the wafer by minus these amounts as described in Example 2, the image shifting may be performed without the compensated spot shifting. Such shifting provides each pupil point with a pupil-coordinate dependent phase. Performing a pupil calibration enables one to know these phases. With that knowledge, both $\beta_n(\vec{k})$ and $\gamma(\vec{k})$ may be extracted using the algorithms described above, and consequently the overlay may be extracted by any of the methods described above in Example 2.

Figure 9B:
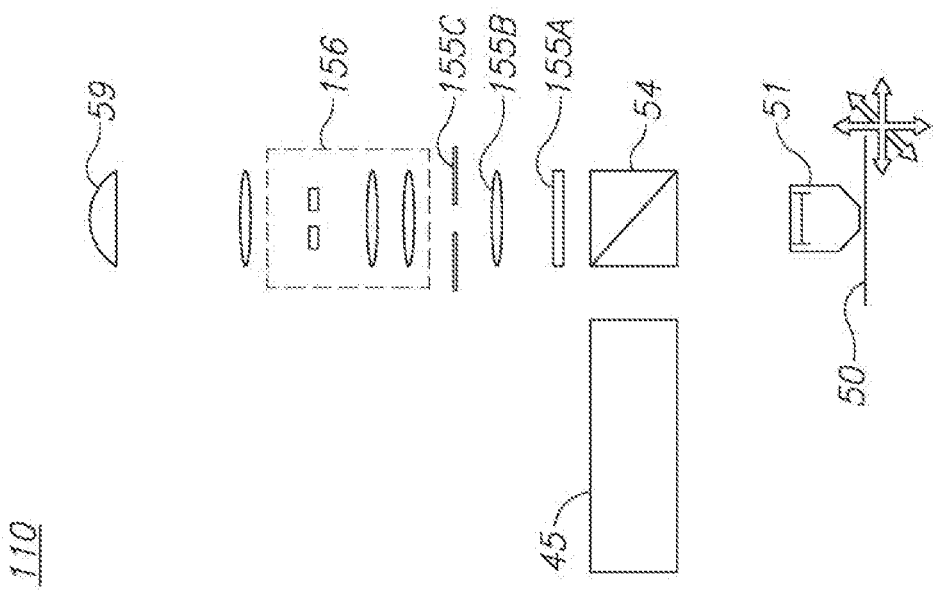
FIG. 9B is a high level schematic illustration of a metrology system with uncompensated field shifting, according to some embodiments of the invention.
Figure 9A:
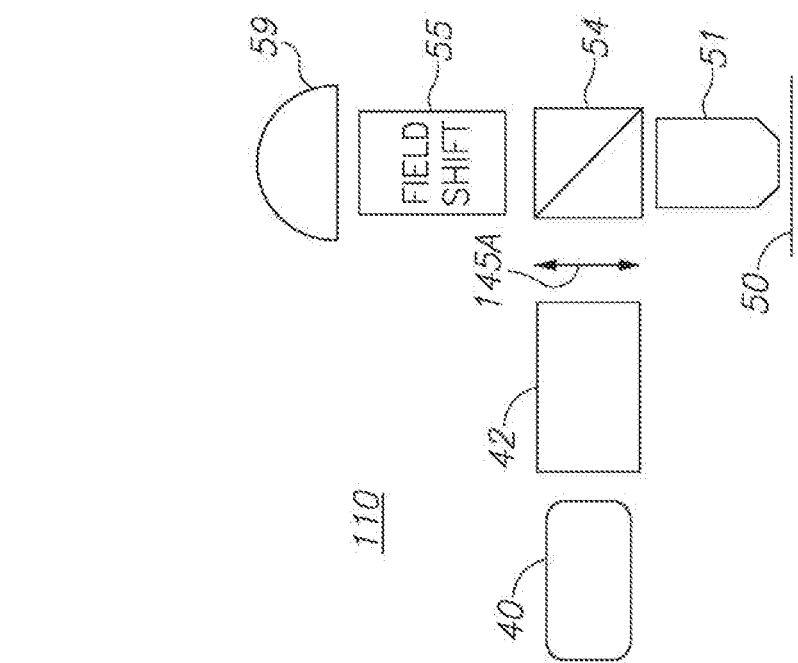
FIG. 9A is a high level schematic illustration of a metrology system that may be adapted to measure targets in the uncompensated field shifts example, according to some embodiments of the invention.

FIG. 9A is a high level schematic illustration of a metrology system 110 that may be adapted to measure targets 100 in the uncompensated field shifts example, according to some embodiments of the invention. In the illustrated example, collection arm 55 may comprise field shift module 156 without any field shift module in the illumination arm (see only lens 145A). Field shift module 156 may comprise, beside the field shift mechanism, all relevant components and systems (e.g. optics and mechanics) to enable correct imaging of the required signal on the detector.

FIG. 9B is a high level schematic illustration of metrology system 110 with uncompensated field shifting according to some embodiments of the invention. In the uncompensated field shifting example, the target cell image is shifted, effectively, without moving the spot. Field shifting may be carried out according to similar principles as illustrated in FIGS. 8A-8F and the optical elements may be built to facilitate both x and y targets at the same time as well as all cells at the same time, e.g. for a four cell target.

Example 5—Phase Shifts

In certain embodiments, method 500 comprises measuring pupil images corresponding to several values of illumination phase (stage 544), by setting $\varphi_2=0$, Offset=0 and the illumination phases to a predetermined set of N values $\varphi_{a=1}=\varphi_{1,2, \ldots, N}$. The measured corresponding N pupil images are used to extract the overlay in any of the algorithms described in the sections of Example 2 presented above.

In certain embodiments, these measurements may be carried out with polarized or un-polarized light. If polarized, the polarization of beams (1) and (2) can be identical or different, and if the two polarizations are orthogonal, a polarizer may be used at collection arm 55. The polarization of the beams may be linear or polar (radial/azimuthal).

FIG. 10A is a high level schematic illustration of a metrology system 110 that may be adapted to measure targets 100 in the phase shifts example, according to some embodiments of the invention. In the illustrated example, illumination arm 45 may comprise a phase shift module 147. Phase shift module 147 may comprise, beside the phase shift mechanism, all relevant components and systems (e.g. optics and mechanics) to enable correct illumination of target 100 on substrate 50 and collection arm 55 includes all required components and systems to enable correct imaging of the required signal on the detector. Phase shift module 147 is arranged to generate a global phase difference between the two spots (illumination beams), either in illumination arm 45 or in collection arm 55, as exemplified here and in the following Examples 6-8. Beam phases may be shifted by various means, e.g., by introducing an index of refraction based phase modulator to one of the beams. For example, phase shift module 147 may be based on any of the Pockels effect or the Kerr effect, and may comprise e.g., $LiNbO_3$ modulators, fiber based modulators, free space modulators, waveguide modulators, optical path based modulators (e.g., optical delay lines) or a phase SLM (Spatial Light Modulation), possibly for finer tuning (realized e.g. by MEMS, liquid crystals etc.).

Example 6—Phase Shifts with a Polarized Collection Field Stop

FIG. 10B is a high level schematic illustration of a metrology system 110 that may be adapted to measure targets 100 with a polarized collection field stop, according to some embodiments of the invention.

In certain embodiments, method 500 comprises using mutually orthogonal polarized illumination beams and (stage 550) and configuring the collection field stop to have respective polarizers to separate the illumination beams (stage 552) to improve the accuracy of overlay measurements by reducing the leakage of light from the tail of one beam falling onto the other cell and vice-versa.

At the collection field stop plane (CFS 155C) plane, CFS 155C may be divided into two parts 187A, 187B, namely CFS part 187A that is aligned with target cell 101A, on which respective illumination beam 169A is incident, and CFS part 187B that is aligned with target cell 101B, on which respective illumination beam 169B is incident. Collection field stop 155C may have a polarizer 155G with a polarization angle that is parallel to the polarization axis in CFS part 187A and a polarizer 155H with a polarization angle that is parallel to the polarization axis in CFS part 187B. This "polarized CFS" reduces the leakage of light from the tail of illumination beam 169A falling onto cell 101B and vice-versa. In addition, a polarizer 155I may be set before the pupil detection plane. The polarization angle of polarizer 155I may be optimized in accordance to sensitivity, to achieve optimal contrast of the cross polarized incident beams. It is noted that the input polarization need not be linear, and one can use, for example, radial polarization in beam 169A and azimuthal polarization in beam 169B, with respective polarizers in the CFS parts 187A and 187B. For example, parts 187A, 187B may be two halves of CFS 155B with orthogonal polarizations. In certain embodiments, a complete control of the polarization distribution may be achieved in illumination arm 45 and/or in collection arm 55, e.g., by use of a polarization sensitive SLM such as a liquid crystal device. In certain embodiments, CFS 155C may be apodized. In certain embodiments, the polarization control may be carried out in a single plane as the aperture limit or in a different plane (e.g., either another field conjugate plane or an intermediate plane).

In certain embodiments, multiple polarizers may be used in the collection path, e.g., collection arm 55 may be duplicated after collection field stop 155C into two collection arms (i.e. two polarizers 155H and two pupil cameras 59 may be placed at the end of the two collection arms). Importantly, one needs to tune polarizer no. 1 to have angle α and polarizer no. 2 to have angle –α (with α chosen to optimize overlay sensitivity). To understand why, consider the interference of light coming from beam no. 1 (which is, for example, X-polarized in illumination) and reflecting off cell no. 1, with the tail of beam no. 2 (which, in this example, is Y-polarized in illumination), that is also reflected off cell no. 1, and that was rotated into an X-polarized light. Because this interference term does not contain overlay information it causes overlay inaccuracy. Interestingly, however, this interference term does not flip sign under the transformation α→–α. In contrast, the interference terms which do contain overlay information switch their sign when α does. Therefore, if the signals are subtracted from the two cameras 59, a portion of the signal inaccuracy is removed and the overlay accuracy is improved.

Example 7—Collection Phase Shifts

In certain embodiments, method 500 comprises shifting phases of the reflected beams in the collection arm (stage 555) by placing a phase modulator, which induces the phase onto one of the beams, into collection arm 55 (instead of in illumination arm 45 as described in Example 5). Extraction of the overlay is equivalent to that explained above in the "compensated field shifts" and the "phase shifts" Examples 2 and 5. As in former examples, the beams may be polarized to improve the accuracy of the measurements accuracy and the collection filed stop may comprise respective polarizers as explained in Example 6. The input polarization need not be linear polarizations, and one can use, for example, radial polarization in beam (1) and azimuthal polarization in the other.

FIG. 10C is a high level schematic illustration of a metrology system 110 that may be adapted to measure targets 100 in the collection phase shifts example, according to some embodiments of the invention. In the illustrated example, collection arm 55 may comprise a phase modulation mechanism 157 associated with CFS 155C.

Example 8—Pupil Phase Shifts

In certain embodiments, method 500 comprises shifting phases of the reflected beams in the pupil plane (stage 560). A phase inducer (for example, a rotating plate with N wedges, each corresponding to a specific phase shifts) is placed in a pupil plane on collection arm 55. In certain embodiments, phase shifts may be applied with respect to the polarization of the beam (stage 562). The phase inducer may be controlled to induce phase-shifts only to one polarization (for example, only to an X-polarized light), and in a known way that depends on the plate's properties and the light's wavelength. In certain embodiments, different phases may be induced for the ±1 diffraction orders and/or for different diffraction orders (stage 564). The phase inducer may be controlled to induce a different phase onto the +1$^{st}$ diffracted light and the −1$^{st}$ diffracted light, with relative phases $\varphi_{1,2,\ldots,N}$. To extract the overlay from the corresponding N pupil images, any one of the steps and algorithms described above in Example 2 (compensated field shifts) may be used.

With respect to phase shifts disclosed in any of the above examples, in certain embodiments, continuous phase shifts may be induced and the shifts may be made discrete by the pixel light integration procedure at detector 59 (stage 566).

With respect to phase shifts disclosed in any of the above examples, in certain embodiments, method 500 comprises applying a per-pixel weight during the extraction of the overlay (stage 570). In certain embodiments, the pixel weights may be chosen to optimize the signal to noise ratio of the overlay measurement on each pixel (stage 572) and in certain embodiments, the pixel weights may be used to perform a weighted average of the overlay across the pupil (stage 574).

In certain embodiments, the per-pixel weights may be used to provide direct and on-the-fly accuracy metrics. Since side-by-side SCOL involves two beams falling on two different gratings, the beam on one of the gratings may be turned off to measure the pupil image and conclude whether there is a per-pixel asymmetry. If such asymmetry exists, it is cause for an overlay inaccuracy, which may thus be identified, evaluated and reported. In all Side-by-side SCOL technologies, excluding the multiple measurement technology (Example 1) and algorithms II and III (in Example 2), the overlay information is found in the phase of the complex differential signal Z=D1+iD2. In particular, the overlay is extracted from the difference in the phases that correspond to Z(p) and Z(p') that are located at pupil point p and p', where p' is the 180° rotation of p (see FIG. 5A). Further information, however, may be found in the amplitude of Z(p) and Z(p'). Specifically, if no inaccuracy is present, these amplitudes should be equal. Based on this simple observation, one can optimize a per-pixel weight which decreases as |Z(p)| becomes more different than |Z(p')| and provide the customer with a confidence level in the overlay measurement, which by itself may be used as an indicator for global target noise, grating asymmetry, target-size related inaccuracy, etc. In certain embodiments thus, method 500 may comprise using either the per-pixel asymmetry with respect to an illumination of one of the periodic structures and a comparison of the signal amplitudes at opposite pixels to estimate inaccuracies.

In any of the disclosed examples, method 500 may comprise in certain embodiments, calibrating the pupil using the overlay measurements (stage 580). Several of the algorithms presented above involve the averaging of a function $f(\vec{k})$ across the plus and minus 1$^{st}$ order circles in a symmetric way $(f(\vec{k})+f(-\vec{k}))$. This requires that the points $A_\pm$ on the plus and minus 1$^{st}$ order circles on the detector, in which $\vec{k}=0$, are known. Assuming that the center of the whole collection pupil $A_0$ is known, (which is imperative in all 1$^{st}$ order SCOL technologies), the points $A_\pm$ can be obtained if an angle θ between the detector's coordinate system and the grating-cell's coordinate system is known. The following options exemplify methods of estimating θ.

A first option is to apply a mathematical alignment in which the angle θ is measured using a field camera in the normal procedure, by measuring the tilt between two grating cells that are very far apart on the wafer. In addition, a lens may be inserted before the field camera, so to make it into a pupil camera, on which the overlay measurement in done. This makes sure that the measured θ is between the grating cell coordinate system in the field plane and the coordinate system of the pupil plane on the detector.

A second option is to apply a pupil TIS (tool induced shift) calibration, namely by measuring a TIS map from the measurement of the overlay of a single grating and subtracting the TIS map from the actual overlay pupil map. As the angle θ introduced a purely TIS error which is only a function of θ and the distance between the spots and is a purely geometrical contributor, the proposed TIS calibration removes the error introduced by the angle θ.

In any of the disclosed examples, method 500 may comprise in certain embodiments, modulating the beam amplitudes by apodizer(s) in pupil plane and/or in field plane (stage 590). These apodizers may, for example, take the form of the Blackman apodizers, or any other type of modulation of the light amplitude in the corresponding plane.

FIG. 10D is a high level schematic illustration of a metrology system 110 that may be adapted to measure targets 100 in the pupil phase shifts example, according to some embodiments of the invention. In the illustrated example, a phase modulating mechanism 158 is positioned at pupil plane. The illumination and collection arms 45, 55 include all required components and systems to enable correct illumination of target 100 on substrate 50 and collection of the required signal on detector 59, accordingly.

In certain embodiments, the phase modulation may be polarization sensitive. Such feature could be achieved for example by using a birefringent electro-optic material (e.g. $LiNbO_3$) to apply the phase shift only for one of the polarizations that pass through the material. The geometrical arrangement of the component could be used to facilitate a different phase shift for different orders in the pupil (e.g. +1 and −1 diffraction orders).

Combinations of Technologies

This section illustrates some non-limiting examples for implementing system 110 according to the principles disclosed above and in combination with systems disclosed elsewhere in order to achieve reciprocal enhancement of their features. FIGS. 11A-D are high level schematic illustrations of such metrology systems 110, according to some embodiments of the invention.

FIG. 11A is a high level schematic illustration of a metrology system 110 that combines spot splitting with optical offsets or phase modulations (Examples 2-8 presented above), according to some embodiments of the invention.

FIG. 11B is a high level schematic illustration of a metrology system 110 that enables alternation between using spot splitting with phase shifting and using a de-coherence module 191 in illumination arm 45, according to some embodiments of the invention. Module 191 in illumination arm 45 comprises two arms with two alternate beam paths split by beam splitter 42A. One sub-beam goes through an aperture stop and an illumination field stop and then through a spot splitting and phase shift module (optionally with power balancing) 42B, 147. Another sub-beam is collimated and passed through a de-coherence module 191, which may comprise an aperture stop and a contrast enhancer associated with an illumination field stop. De-coherence module 191 enables imaging metrology of diffraction orders as an additional feature of system 110. The optical paths of the two sub-beams are re-combined at a beam splitter 193 to allow switching between de-coherent illumination and split-spot phase shifted illumination.

FIG. 11C is a high level schematic illustration of a metrology system 110 that combines spot splitting and phase shifting with a near field technologies (illustrated e.g., in WIPO Patent Document No. PCT/US13/47682, incorporated herein by reference in its entirety), according to some embodiments of the invention. In such embodiments, the optical interaction of illumination beams 169A, 169B with target cells 101A, 101B is carried out in the near-field and may utilize near field effects to enhance various features of the measurements that result from the side by side targets and optimize various aspects of the overlay extraction. A waveplate 52 may be introduced before objective 51 to enhance sensitivity and increase information content.

In certain embodiments, metrology system 110 with side by side targets may also be used for imaging (instead of scatterometry overlay measurements) or may be integrated with current SCOL systems and targets. Also, any combination of the above examples may be used to enhance measurements, as illustrated in FIG. 14.

FIG. 11D is a high level schematic illustration of a metrology system 110 that combines spot splitting with phase modulation, de-coherence system 191 and a near field technologies, according to some embodiments of the invention. System 110 in these embodiments combined features of systems 110 from FIGS. 11B and 11C.

Multiple Side by Side Targets

Current overlay measurement technologies that rely on scatterometry require the manufacture of "grating-over-grating" targets that comprise two gratings in the same direction and of the same pitch in the respective layers between which one wishes to measure the overlay error. Current SCOL technologies use two such targets to measure the positive and negative first diffraction, so that measuring overlays among N layers generally require ca. $N^2$ targets (e.g., $N(N-1)/2$).

FIG. 12A-12C are high level schematic illustration of metrology targets 100 with multiple cells, according to some embodiments of the invention. Illustrated target 100 may comprise N cells at N different layers, in the non-limiting illustrated example N=6 with target 100 comprising cells 101A, 101B, 101C, 101D, 101E and 101F positioned at six different layers, each having periodic structures 85 with the same pitch. Target 100 enables the measurement of overlay between the N layers processed in lithography during semiconductor manufacture to be performed accurately on metrology structures of reduced dimensions compared with the state of the art by using the side-by-side overlay scatterometry paradigm.

In the side by side paradigm, targets 100 use the wafer area in a much more efficient way to yield measurement results. In the illustrated example, cells 101 may be designated by an arbitrary relative position vector $\vec{r}$ and the spot splitting may be dependent on r to allow measuring the overlay error using any pair of cells 101. For example, FIG. 12B illustrates extracting the overlay for measurements using cells 101A, 101B, while FIG. 12C illustrates extracting the overlay for measurements using cells 101C, 101F.

Taking a non-limiting example of using the side by side paradigm as implementing a phase shift interferometer (see e.g., Example 5), a given spatial distribution of N single gratings 85 at N layers on the wafer (e.g., all with the same grating pitch 103, and the same grating direction 102), any pair of cells 101 may be used to measure the relative overlay.

The real-estate (used wafer area) of target 100 for measuring overlays among N layers is thus proportional to N, in contrast to current SCOL technologies which require a real estate that is proportional to $N^2$.

Advantages of the Proposed Side by Side Technology with Respect to SCOL

The following are some of the advantages of certain embodiments of the invention with respect to using the proposed side by side technology in scatterometry overlay (SCOL) measurements.

Zero algorithmic inaccuracy. Current SCOL technologies are fundamentally based on the assumption that the way the SCOL signal depends on the programmed offset and the induced offset is a simple series in cos (2πm(programmed offset+overlay)/Pitch) and sin (2πm(programmed offset+overlay)/Pitch) with m any integer number. Depending on details, current SCOL technologies measure only a limited number of SCOL signals (those that correspond to a limited number of values for the total offset). This fact necessarily means that the overlay measurement involves a generic inaccuracy. This inaccuracy depends on many things (like the specific stack, the programmed offset, the overlay, the target design, and the algorithm), and can reach a few nanometers in problematic stacks and a few angstroms in others. In addition, finite target size effects cause deviations of the signal form from a sum of sines and cosines. This causes additional algorithmic inaccuracy which increases as the target size decreases. As explained in the previous sections pertaining to the specifics of the different side-by-side SCOL technology, the algorithmic inaccuracy of all side-by-side technologies is zero.

Low sensitivity to illumination asymmetry. Current first order SCOL technologies extract the overlay from the difference in intensity at pupil pixel p and the 180 deg rotated pupil pixel p'. In the presence of illumination asymmetry, this intensity difference reflects both the overlay and the illumination asymmetry itself. This causes TIS and TIS3S, which is directly proportional to the per-pixel illumination asymmetry. To overcome this and decrease TIS and TIS3S, current first order SCOL technologies use a variety of prescriptions to cancel out the TIS and TIS3S due the illumination asymmetry that involve a variety of error-prone calibrations to correct for illumination asymmetry. All these prescriptions involve errors that are best avoided. In most side by side SCOL technologies (Algorithms II and III excluded), two differential signals are initially extracted from the 1st and −1st order, and then, two phases which contain the overlay are extracted from these two signals. The overlay is contained in the difference between these two phases. Importantly, because the overlay is contained in phase information which is probed directly by the technology and for each order separately, there is no dependence on illumination asymmetry and the resulting TIS and TIS3S is zero.

Good overlay sensitivity. The overlay sensitivity of current SCOL technologies is partly determined by the number N of the signals collected from the target, which is equal to the number of cells that are printed on the target. It also depends on the value of the programmed offsets printed by the scanner. The number N in current SCOL technologies (like 1st order and 0th order SCOL) is limited by cost of ownership considerations, and for example at 1st order SCOL one usually sets N=2 and in 0th order SCOL one sets N=4. The value of the programmed offsets is determined by optimizing a balance between sensitivity and algorithmic accuracy. Because Side-by-side technologies have zero algorithmic inaccuracy, and because the N signals obtained in the side by side paradigm all come from the same two cells (excluding Example 3—wafer shifts), but have differing illumination/collection configurations, then for the same number of physical printed cells, the sensitivity is much optimized compared to current SCOL technologies.

Low sensitivity to target asymmetry. Current first order SCOL technologies are very sensitive to grating asymmetry. In particular, while a grating asymmetry of a few percentages (in, for example, the side-wall-angles) can cause a few nanometers of an ambiguity in the definition of the overlay, current 1st order SCOL technologies tend to amplify these few nanometers to much larger inaccuracy, reaching tens of nanometers on occasions. The basic reason for this amplification is that the overlay signal in current first order SCOL technologies is extracted from differences of intensities and so it is sensitive to the asymmetry of the amplitude of the electromagnetic fields induced by the grating asymmetry.

In contrast to that, most side-by-side SCOL technologies (excluding Algorithm II and III), are only sensitive to the phase asymmetry generated by the grating asymmetry, and this phase asymmetry is nothing but the overlay ambiguity. Thus, excluding Algorithm II and III, side by side SCOL technologies have a minimal sensitivity to global target asymmetry.

Low sensitivity to target noise. Current SCOL technologies can be very sensitive to random target noise (for example, to random induced topography). Such target imperfection is caused by the incompatibility of the process to the target pitch, especially when a grating over grating SCOL stack is printed. Also, in current SCOL technologies, if one wishes to increase overlay sensitivity in current SCOL technologies, and/or reduce the algorithmic inaccuracy, one is led to printing more grating-over-grating cells with additional programmed offsets, which lead to an increased level of target noise, and so to degraded accuracy. Since side-by-side SCOL technologies are not grating-over-grating targets, they are expected to be much more process compatible. In addition, an increase of the number of signals N (so to improve sensitivity or reduce effects of slowly oscillating system noise, for example) does not increase target-noise related inaccuracy because all N signals are taken from the same physical cells (here we exclude the "wafer shifts" technology).

Zero sensitivity to intra-target process variation. Current SCOL technologies assume that the only difference between the cells contained in one target are the programmed offsets. Even in the absence of random target noise this assumption may be broken by intra-target process variations. These process variations cause a cell-to-cell variability in the reflectivity which is additional to the variation due to the programmed offset. In side by side SCOL, there is only one cell on each layer and so intra-target process variations are a non-issue (excluding the Example 3—wafer shifts).

Low real-estate area for given sensitivity: For the same reasons explained above, increasing the number of signals N by a factor f in current SCOL technologies increases target size by roughly f. In contrast, the target size in all side-by-side technologies is independent on N. In addition, and as explained above, there is a possibility to simultaneously measure overlays along the X and Y directions, with only two cells, while the minimal number of cells that are required in current SCOL technologies is four. Finally, to measure the overlay between multitudes of layers in current SCOL technologies requires a grating over grating SCOL target for each of the layers' pairs. In contrast, in side by side SCOL, a single grating for each layer is required.

Low sensitivity to fully correlated noise. Current SCOL technologies are very sensitive to fully correlated noise, and, to avoid inferior TMU and accuracy, the tolerance on fully correlated system noise is quite tight. In contrast, in side by side SCOL, the fully correlated noise contribution to precision is minimal because, as a result of the inter-beam distance, the signal on the pupil is strongly oscillating with the pupil coordinate. This causes the influence of the fully correlated noise to be much reduced from its "naive" value.

The side by side paradigm also allows for performance optimizations which arise from the fact that side by side SCOL involves two coherent beams and so there is a larger space of system parameters to be optimized over. These kinds of performance optimizations are thus not possible in current SCOL technologies. (1) Per-beam light intensity tuning. In stacks where the contrast is sub-optimal (because one grating is more reflective than the other), the light level of one beam may be tuned relative to the other beam, to shed less light on the more reflective layer. This was shown in simulations to enable the measurements of certain challenging stacks. (2) Using cross-polarized beams and optimizing the analyzer angle. For the same stacks where the contrast is sub-optimal, and if one uses one of the side by side technologies that involve cross-polarized beams, the angle of the final polarizer which enables the interference between the cross-polarized beams, can be tuned to enable optimal contrast. In addition, the choice of the polarization axes along which the incident beams are polarized can be used as a knob to optimize the performance of the side by side technology.

In the above description, an embodiment is an example or implementation of the invention. The various appearances of "one embodiment", "an embodiment", "certain embodiments" or "some embodiments" do not necessarily all refer to the same embodiments.

Although various features of the invention may be described in the context of a single embodiment, the features may also be provided separately or in any suitable combination. Conversely, although the invention may be described herein in the context of separate embodiments for clarity, the invention may also be implemented in a single embodiment.

Certain embodiments of the invention may include features from different embodiments disclosed above, and certain embodiments may incorporate elements from other embodiments disclosed above. The disclosure of elements of the invention in the context of a specific embodiment is not to be taken as limiting their use in the specific embodiment alone.

Furthermore, it is to be understood that the invention can be carried out or practiced in various ways and that the invention can be implemented in certain embodiments other than the ones outlined in the description above.

The invention is not limited to those diagrams or to the corresponding descriptions. For example, flow need not move through each illustrated box or state, or in exactly the same order as illustrated and described.

Meanings of technical and scientific terms used herein are to be commonly understood as by one of ordinary skill in the art to which the invention belongs, unless otherwise defined.

While the invention has been described with respect to a limited number of embodiments, these should not be construed as limitations on the scope of the invention, but rather as exemplifications of some of the preferred embodiments. Other possible variations, modifications, and applications are also within the scope of the invention. Accordingly, the scope of the invention should not be limited by what has thus far been described, but by the appended claims and their legal equivalents.

What is claimed is:

1. A metrology target comprising:
   at least three cells, wherein the at least three cells comprises a first cell, a second cell, and a third cell, wherein the first cell comprises a first parallel periodic structure disposed at a first layer, wherein the second cell comprises a second parallel periodic structure disposed at a second layer, and the third cell comprises a third parallel periodic structure disposed at a third layer, wherein the first layer is different from the second layer and the third layer, wherein the second layer is different from the third layer, wherein each of the first parallel periodic structure, the second parallel periodic structure and the third parallel periodic structure include a same pitch,
   wherein the pitch of the first parallel periodic structure, the second parallel periodic structure, and the third parallel periodic structure is uniform across each of the first parallel periodic structure, the second parallel periodic structure, and the third parallel periodic structure,
   wherein a perimeter of the metrology target is defined by one or more cell edges, wherein at least one of the first parallel periodic structure, the second parallel periodic structure, or the third parallel periodic structure is disposed within the perimeter of the metrology target such that it is central with respect to the one or more cell edges,
   wherein the pitch of the first parallel periodic structure and the pitch of the second parallel periodic structure is uniform across the first cell,
   wherein the first cell overlaps with at least one of the second cell or the third cell,
   wherein the first cell, the second cell, and the third cell are individually invariant with respect to a selected rotational transformation about an axis perpendicular to at least one of the first cell, the second cell, or the third cell.

2. The metrology target of claim 1, wherein the selected rotational transform is a 180° rotation about an axis perpendicular to at least one of the first cell, the second cell, or the third cell.

3. The metrology target of claim 1, wherein the first cell includes at least two parallel gratings invariant under a 180° rotation about an axis perpendicular to the first cell, wherein the second Cell includes at least two parallel gratings invariant under a 180° rotation about an axis perpendicular to the second cell.

4. The metrology target of claim 1, wherein at least one of the first parallel periodic structure, the second parallel periodic structure, or the third parallel periodic structure comprises one or more gratings.

5. The metrology target of claim 1, wherein at least one of the first parallel periodic structure, the second parallel periodic structure, or the third parallel periodic structure comprises at least two parallel gratings, wherein the at least two parallel gratings are invariant under a 180° rotation about an axis perpendicular to the first cell.

6. The metrology target of claim 1, wherein the metrology target is configured as a scatterometry overlay (SCOL) target.

7. The metrology target of claim 1, wherein the metrology target is configured as an optical critical dimension (OCD) target.

8. The metrology target of claim 1, wherein the first parallel periodic structure, the second parallel periodic structure, and the third parallel periodic structure are parallel.

9. The metrology target of claim 1, wherein the first parallel periodic structure is orthogonal to at least one of the second parallel periodic structure or the third parallel periodic structure.

10. The metrology target of claim 9, wherein the first parallel periodic structure is orthogonal the second parallel periodic structure, and wherein the second parallel periodic structure is orthogonal to the third parallel periodic structure.

11. The metrology target of claim 1, wherein the first parallel periodic structure and the second parallel periodic structure are oriented with respect to one of two directions of the metrology target.

12. The metrology target of claim 1, wherein the selected rotational transform is a 180° rotation about an axis perpendicular to at least one of the first cell, the second cell, or the third cell.

13. The metrology target of claim 1, wherein the pitch of the first parallel periodic structure is equivalent to the pitch of the second parallel periodic structure.

14. The metrology target of claim 13, wherein the pitch of the third parallel periodic structure is equivalent to the pitch of the first parallel periodic structure and the second parallel periodic structure.

15. The metrology target of claim 1, wherein the first cell overlaps with both the second cell and the third cell.

16. The metrology target of claim 1, wherein the first parallel periodic structure, the second parallel periodic structure, and the third parallel periodic structure are disposed within the perimeter of the metrology target such that each of the first parallel periodic structure, the second parallel periodic structure, and the third parallel periodic structure are central with respect to the one or more cell edges.

17. The metrology target of claim 1, wherein the metrology target including the first cell, the second cell, and the third cell is invariant with respect to a third selected rotational transformation about an axis perpendicular to the first cell, the second cell, and the third cell.

18. The metrology target of claim 1, further comprising at least one additional cell disposed in at least one of the first layer, the second layer, or the third layer, wherein the at least one additional cell comprises at least one additional periodic structure.

19. The metrology target of claim 1, further comprising a fourth cell disposed at a fourth layer, wherein the fourth layer is different from the first layer, the second layer, and the third layer.

20. The metrology target of claim 19, wherein the first cell at least partially overlaps the fourth cell.

* * * * *